Figure 1:
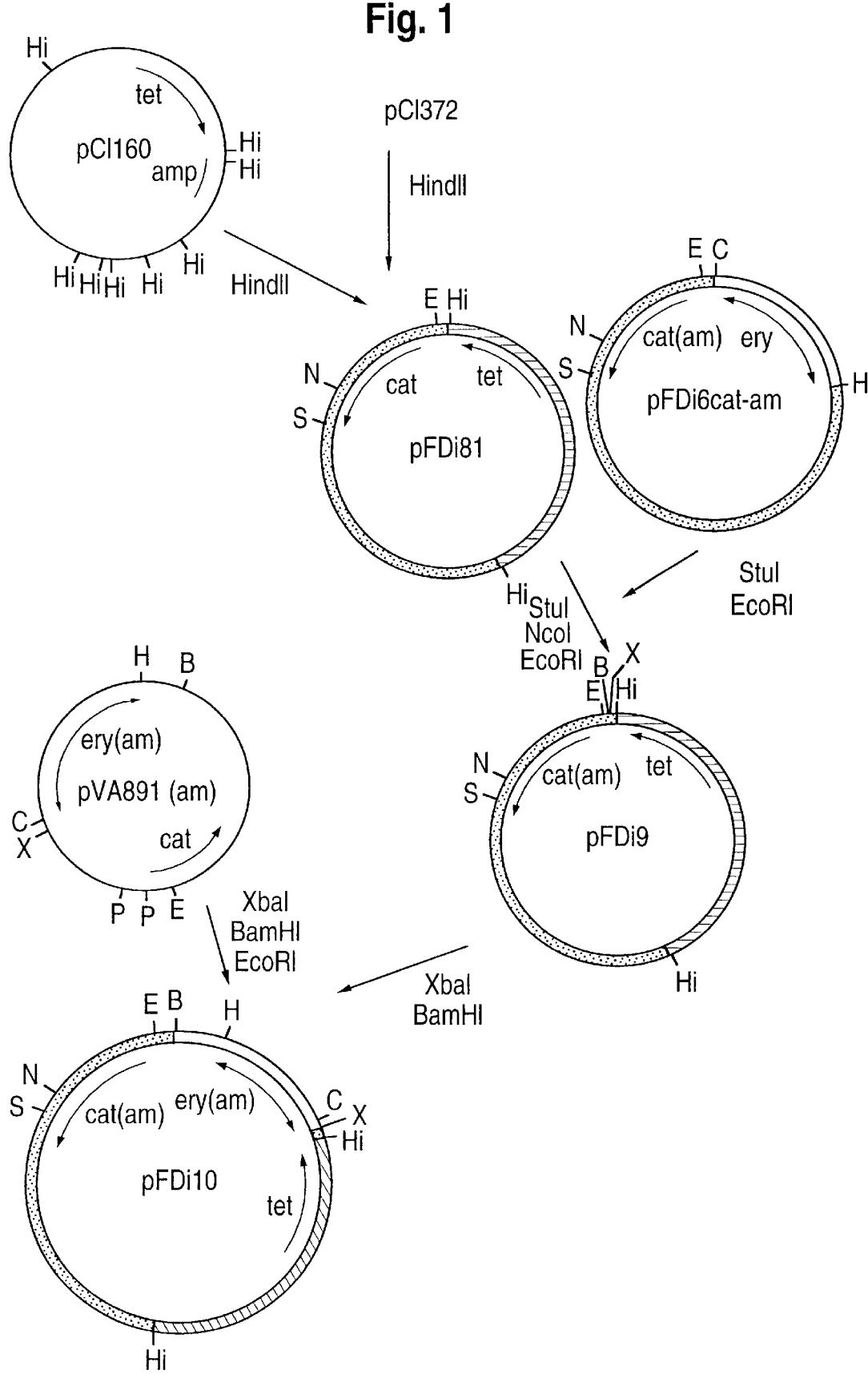

US005866385A

United States Patent [19]
Dickely et al.

[11] Patent Number: 5,866,385
[45] Date of Patent: *Feb. 2, 1999

[54] LACTIC ACID BACTERIAL SUPPRESSOR MUTANTS AND THEIR USE AS SELECTIVE MARKERS AND AS MEANS OF CONTAINMENT IN LACTIC ACID BACTERIA

[75] Inventors: Françoise Dickely, Obernai; Eric Johansen, Hørsholm; Dan Nilsson, Copenhagen; Egon Bech Hansen, Brønshøj, all of Denmark

[73] Assignee: CHR. Hansen A/S, Hoersholm, Denmark

[ * ] Notice: The term of this patent shall not extend beyond the expiration date of Pat. No. 5,691,185.

[21] Appl. No.: 535,092

[22] PCT Filed: Oct. 7, 1994

[86] PCT No.: PCT/DK94/00376

§ 371 Date: Dec. 5, 1995

§ 102(e) Date: Dec. 5, 1995

[87] PCT Pub. No.: WO95/10621

PCT Pub. Date: Apr. 20, 1995

Related U.S. Application Data

[63] Continuation-in-part of Ser. No. 242,098, May 13, 1994, Pat. No. 5,691,185, which is a continuation-in-part of Ser. No. 133,390, Oct. 8, 1993, abandoned.

[51] Int. Cl.[6] .............................. C12N 1/21; C12N 15/74; A23C 9/123; A23B 7/10
[52] U.S. Cl. .................................. 435/172.3; 435/252.1; 435/252.3; 435/252.9; 435/320.1; 426/39; 426/42; 426/52; 426/56
[58] Field of Search .......................... 435/252.3, 252.9, 435/252.1, 320.1, 172.3; 426/39, 42, 52, 56

[56] References Cited

U.S. PATENT DOCUMENTS 4,687,737  8/1987  Sharp et al. ........................... 435/69.1

FOREIGN PATENT DOCUMENTS 0 309 961  4/1989  European Pat. Off. .
0 355 036  2/1990  European Pat. Off. .

OTHER PUBLICATIONS

Schmieger et al., Genet. Res. 52 (3): 163–168, 1988.
Andachi et al., "Condon Recognition Patterns as Deduced from Sequences of the Complete Set of Transfer RNA Species in *Mycoplasma capricolum*", J. Mol. Biol., 1989, 209:37–54.
Austin et al., Plasmid, 1983, 10:73–81.
Campbell, "The Steric Effect in Lysogenization by Bacteriophage Lambda. I. Lysogensation by a Partially Diploid Strain of *E. coli* K12", Virology, 1965, 27:329.
Clark, et al., "DNA Replication and the Division Cycle in *Escherichia coli.*", J. Mol. Biol., 1967, 23:99–112.

Demerec, et al., "A Proposal for a Uniform Nomenclature in Bacterial Genetics", Genetics, 1966, 54:61–76.
Deno, et al., "The Nucleotide Sequence of tRNA Ser (GCU) and tRNA (UUG) Genes from Tabacco Chloroplasts", Nucleic Acids Res., 1983, 11:8407–8414.
Eggertson, et al., "Transfer Ribonucleic Acidmediated Suppression of Termination Condons in *Escherichia coli.*", Microbiol. Rev., 1988, 52:354–374.
M.J. Gasson, "Plasmid Complements of *Streptococcus lactis* NCDO712 and Other Lactis Streptococci after Protoplast Induced Curing", J. Bacteriol., 1983, 154:1–9.
Hanic–Joyce, et al., "Processing of Transfer RNA Precursors in a Wheat Mitochondrial Extract", J. Biol. Chem., 1990, 265:13782–13791.
Hayes, et al., "Identification of the Ninimal Replicon of *Lactococcus lactis* Subsp. *lactis* UC317 Plasmid pC1305", Appl. Environ. Microbiol., 1990, 56:202–209.
Hill, et al., "Cloning and Characterization of the Tetracycline Resistance Determinant of and Several Promoters from within the Conjugative Transposon Tn919", Appl. Environ. Microbiol., 1988, 54:1230–1236.
Hiratsuka, et al., "The Complete Sequence of the Rice (*Oryza sative*) Chloroplast Genome: Intermolecular Re–combination Between Distinct tRNA Genes Accounts for a Major Plastid DNA Inversion During the Evolution of Cereals", Mol. Gen. Genet., 1989, 217:185–194.
Holo, et al., "High–frequency Transformation, by Electroporation, of *Lactococcus lactis* subsp *cremoris* Grown with Glycine in Osmotically Stabilized Media.", Appl. Environ. Microbiol., 1989, 55:3119–3123.
Israelsen, et al., "Insertion of Transposon Tn917 Derivatives into the *Lactococcus lactis* subsp *lactis* Chromosome", Appl. Environ. Microbiol., 1993, 59:21–26.
Jahns, et al., "Identification, Cloning and Sequencing of the Replication Region of *Lactococcus lactis* subsp. *lactis* Biovar *diacetylactis* Bu2 Citrate plasmid pSL2", FEMS Microbiol. Lett., 1991, 80:253–258.
Johansen, et al., "Characterization of *Leuconostoc* Isolates from Commerical Mixed–Strain Mesophilic Starter Cultures", J. Dairy Sci., 1992, 75:1186–1191.
Karabin, et al., "Euglena Gracilis Chloroplast Transfer RNA Transcription Units. Nucleotide Sequence Analysis of a tRNA Thr–tRNAGly–tRNAMet–tRNASer–tRNAGln Gene Cluster", J. Biol. Chem., 1983, 258:5512–5518.
Ma, et al., "Nucleotide Sequence of *Chlamydomonas reinhardtii* Mitochondrial Genes coding for tRNA gln (UUG) and tRNA met (CAU)", Nucleic Acids Res., 1989, 17:;1256–1256.

(List continued on next page.)

Primary Examiner—Johnny F. Railey, II
Attorney, Agent, or Firm—Foley & Lardner

[57] ABSTRACT

Methods of isolating nonsense suppressor-encoding lactic acid bacteria, cultures and compositions of lactic acid bacteria and plasmids comprising a gene coding for a nonsense suppressor, and a method of confining extrachromosomal replicons capable of replicating in lactic acid bacteria to lactic acid bacteria.

49 Claims, 8 Drawing Sheets

OTHER PUBLICATIONS

Macrina, et al., "Novel Shuttle Plasmid Vehicles for *Escherichia* —*Streptococcus* Transgenic Cloning", Gene, 1983, 25:145–150.

Maid, et al., "Structure and Expression of a Plasmid–encoded groE1 Homologous Heat–shock Gene in Athermophilic Unicellular Red alga", Curr. Genet., 1992, 21:521–525.

Marsh, et al., "The pIC Plasmid and Phage Vectors with Versatile Cloning Sites for Recombinant Selection by Insertional Inactivation", Gene, 1984, 32:481–485.

Nagano, et al., "Sequence and Transcriptional Analysis of the Gene Cluster *trnQ–zfpA–psaI–ORF231–petA* in pea Chloroplasts", Curr. Genet., 1991, 20:431–436.

Nakajima, et al., "Organisation and Structure of an *E. coli* tRNA Operon Containing Seven tRNA Genes", Cell, 1981, 23:239–249.

Neuhard, et al., "Purines and Pyrimidines. In Neidhardt FC (ed), *Escherichia coli* and *Salmonella typhimurium*",American Society for Microbiology, Washington, DC. 1987, pp. 445–473.

Neuhaus, "Nucleotide Sequence of the Chloroplast Genes fro tRNA Gln and the 4 kD K Polypeptide of Photo–system II from Mustard (S.a.)", Nucleic Acids Res., 1989, 17:444–444.

Nilsson, et al., "Phosphoribosylpyrophosphate Synthetase of *Bacillus subtilis.* Cloning, Characterization and Chromosomal Mapping of the *prs* Gene", 1987, 53:247–255.

Nygaard, "Utilization of Preformed Purine Bases and Nucleosides. In Munch–Petersen A (ed), Metabolism of Nucleotides, Nucleosides and Nucleobases in Microorganisms", Academic Press, Inc., NY, 1983, pp. 27–93.

Oda, et al., "Gene Organization Deduced from the Complete Sequence of Liverwort Marchantia Polymorpha Mitochondrial DNA", J. Mol. Biol., 1992, 223:1–7.

Oda, et al., "Transfer RNA Genes in the Mitochondrial Genome from a Liverwort, Marchantia Polymorpha: the absence of chloroplast–like tRNAs", Nucleic Acids Res., 1992, 20:3773–3777.

Ohyama, et al., "Structure and Organization of Marchantia Polymorpha Chloroplast Genome. I. Cloning and gene identification", J. Mol. Biol., 1988, 203:281–298.

Pittet, et al., "Sequence of an Hexameric tRNA Gene Cluster Associated with rRNA Gene in *Lactobacillus bulgaricus*", Nucl. Acid. Res., 1989, 17:4873.

Ryan, et al., "Cloning of Two Chemically Synthesised Genes for a Precursor to the su$^+$3 Suppressor tRNA$^{Tyr}$ in D. Söll, J.N. Abelson and P.R. Schimmel (eds.) Transfer RNA: Biological Aspects", Cold Spring Harbor Laboratory, Cold Spring Harbor, NY, 1980, pp. 245–258.

Sambrook, et al., "Molecular Cloning: A Laboratory Manual", Cold Spring Harbor Laboratory, Cold Spring Harbor, NY.

Siemeister et al., "Gene for the Plastid Elongation Factor Tu and Ribosomal Protein s7 and six tRNA Genes on the 73 kb DNA from *Astasia longa* that Resembles the Cloroplast DNA of Euglena", Mol. Gen. Genet., 1990, 220:425–432.

Silhavy, et al., "Experiments with Gene Fusions", Cold Spring Harbor Laboratory, Cold Spring Harbor, NY, 1984.

Simoneau, et al., "Nucleotide Sequence of a tRNA Cluster from Mycoplasma pneumoniae", Nucleic Acids Res., 1990, 18:2814.

Thorbjarnadottir, et al., "*Escerichia coli supH* suppressor: Temperature–sensitive missense suppression caused by anticodon change in tRNA$^{ser2}$", J. Bacteriol., 1985, 161:207–211.

Tsudzuki, et al., "Chloroplast DNA of Black Pine Retains a Residual Inverted Repeat Lacking rRNA genes: nucleotide sequence of *trnQ, trnK, psbA, trnI and trnH* and the absence of *rps16*", Mol. Gen. Genet., 1992, 232:206–214.

Wawrousek, et al., "Two Large Clusters with Thirty–seven Transfer RNA Genes Adjacent to Ribosomal RNA Gene Sets in *Bacillus subtilis*", J. Biol. Chem., 1984, 259:3694–3702.

Wolfe, et al., "Rapid revolution of the Plastid Translational Apparatus in a Nonphotosynthetic Plant: loss or accelerated sequence evolution of tRNA and ribsomal protein genes", J. Mol. Evol., 1992, 35:304–317.

Yanase, et al., "Cloning, Sequencing and Characterization of the Intracellular in Envertase Gene from *Zymomonas mobilis*", Agric. Biol. Chem., 1991, 55:1383–1390.

Yaniv, et al., "The Nucleotide Sequences of the Two Glutamine Transfer Ribonucleic Acids from *Escherichia coli*", J. Biol. Chem., 1975, 250:3243–3253.

Von Wright, et al., Appl. Environ. Microbiol., 1990, 56(7):2029–2035.

Sullivan, et al., J. Bactero., 1985, 161:377–384.

Huang, et al., Improved Suppressor tRNA Cloning Vectors and Plasmid–Phage Recombination, in Rodriguez et al, ed., Vector, Butterworths, Boston, USA.

Johansen, et al., "Isolation and Characterization of IS1165 . . . ", Plasmid, 1992, 27:200–206.

Nilsson, et al., "A conserved sequence in tRNA and rRNA promotes of *Lactococcus lactis*", Biochem. Biophys. Acta, 1994.

Ogasawara, et al., "Structure and Organization of rRNA operons in the region of replication origin of the *Bacillus subtillis* chromosome", Nucleic Acid Research, 1983, 11(18):6301–6316.

Pedersen, et al., "Genetic analysis of the minimal replicon of the *Lactococcus lactis* susp. *lactis* biovar *diacetylactis* citrate plasmid", Mol. Gen. Genet., 1994.

Stroman, "Sequence of a gene (lap) encoding a 95.3–kDa aminopeptidase from *Lactococcus lactis* ssp. *cremoris* Wg2", Gene, 1992, 113:107–112.

David, et al., "Plasmid transformation by Electroportation of *Leuconostoc paramesenteroides* and its Use in Molecular Cloning", Appl. Environ. Microbiol., 1989, 55(6):1483–1489.

Dessart, et al., "high Frequency Intergeneric and Intrageneric Conjugal Transfer of Drug Resistance Plasmids of *Leuconostoc*", J. Dairy Science, 1991, 74(9):2912–2919.

Winston, et al., J. Bacteriol., 1979, 137(1):433–439.

Hayes, et al., Appl. Environ. Microbiol., 1990, 56:202–209.

Holo, et al., Appl. Environ. Microbiol., 1989, 55(12):3119–3123.

Pittet, et al., Nucl. Acids. Res., 1989, 17:4873.

Eggertsson, et al., Microbiol. Rev., 1988, 52:354–374.

Fig. 3

```
          10                  30                  50
          .                   .                   .
AATTGCGGACAGTGTCTCTTCATTTGAGGCTGCTTTAGAAGAAGCAATCAAGGAATATAATCT
                      ******      ******                ######

70                  90                  110
          .                   .                   .
ATCTATTTAAAGAGATTATAAAAAATTATTGATATTTCTTTGAAATAAATAAGTTAAAAC
                              *****                    ###### pFDi17&18  pFDi19           150                 170
  |———————|  |—                .                   .
TTGAAATTTATGAGGGTTTTTGGTAAAATATTTCTTGTCGTCATCAAGGCGATCTTGGGGT
*****                         ######                    —————

190                 210                 230
          .                   .                   .
ATAGCCAAGCGGGTAAGGCAAGGGACTTTAACTCCCCTCATGCGTTGGTTCGAATCCAGCTA
—————————————————————————————                   ————————————————

250                 270                 290
          .                   .                   .
CCCCAGTAAAAAAAACTTTAAAGGAAACGTTGTTTCCTTTTTCTTTTTACTAAAAATATGA
—————————————————————————————      <— — — — — —
             — — — — —>
```

Fig. 4

```
          10         20         30         40         50         60
TTTGTATAAATATGCGTTTTTTGTTTAGTTATTCTTATTTCATATTATTTCAGGAAGGT
                                    ******              ********
          70         80         90        100        110        120
AATTAACTATGGTATAAATGAAATTAGATAAGGGAGCGGAGCCATGGCAGAGTGGTAATGC
              ######
          130        140        150        160        170        180
AACGGACTCTAAATCCGTCGAACCCGTGTAAAGCGGGCGCAGGGGTTCAAATCCCCCTTGACT
          190        200        210        220        230        240
CCTTATAAGTAGAGTTCTTATTCTCAACTCTATTATATATAAGAAAAATGATAGTATTGAA
          250        260        270        280        290        300
TACGCTTACTCCTCCTTTCCCTGTATGTATAAGATTACATCAGGAGGTTTTTTATTCAA
                        <-------------    ------->
```

Fig. 5A

Fig. 5B

LACTIC ACID BACTERIAL SUPPRESSOR MUTANTS AND THEIR USE AS SELECTIVE MARKERS AND AS MEANS OF CONTAINMENT IN LACTIC ACID BACTERIA

This application is a national phase application of International application no. PCT/DK94/00376, which is a continuation-in-part of U.S. application Ser. No. 08/242,098, filed May 13, 1994, now U.S. Pat. No. 5,691,185, which is a continuation-in-part of U.S. application Ser. No. 08/133,390, filed Oct. 8, 1993, now abandoned.

FIELD OF INVENTION

The present invention provides useful mutants of lactic acid bacteria or plasmids capable of replicating in lactic acid bacteria, comprising nonsense mutation suppressor-encoding genes, the use of such suppressor genes for confining a replicon to a specific lactic acid bacterium or to a lactic acid bacterium growing in a particular environment and for controlling the number of lactic acid bacterial cells in a particular environment.

TECHNICAL BACKGROUND AND PRIOR ART

In the in vivo synthesis of proteins occurring in the ribosomes, mRNA is translated into polypeptide chains. However, the MRNA codons do not directly recognize the amino acids that they specify in the way that an enzyme recognizes a substrate. Translation uses "adaptor" molecules that recognize both an amino acid and a triplet group of nucleotide bases (a codon). These adaptors consist of a set of small RNA molecules known as transfer RNAs (or tRNAs), each of which is only 70 to 90 nucleotides in length. Such tRNA molecules contain unpaired nucleotide residues comprising a CCA triplet at one end of the molecule and, in a central loop, a triplet of varying sequence forming the so-called anticodon that can base-pair to a complementary triplet in the MRNA molecule, while the CCA triplet at the free 3' end of the molecule is attached covalently to a specific amino acid.

The three nucleotide triplets UAG (amber codon), UGA (opal codon) and UAA (ochre codon) do not code for an amino acid. These signals termed stop codons or "nonsense" codons, are involved in polypeptide chain termination. During translation, two protein factors (R1 and R2) recognize these triplets and effect release of the polypeptide chain from the ribosome-mRNA-tRNA complex.

Occasionally a mutation occurs in a cell resulting in a nonsense codon appearing in the middle of a gene, causing premature chain termination and the production of a protein fragment. Such fragments rarely have enzymatic activity.

The effect of such a nonsense mutation can be reversed or suppressed by a second mutation in a gene coding for a tRNA which results in the synthesis of an altered tRNA molecule. Such an altered tRNA recognizes a nonsense codon and inserts an amino acid at that point in the polypeptide chain. The mutated tRNA-encoding gene is termed a suppressor gene and the altered nonsense mutation-suppressing tRNA which it encodes is generally referred to as a nonsense or termination suppressor. Such termination suppressors may be derived by single, double or triple base substitutions in the anticodon region of the tRNA.

Termination suppressors were first detected in *E. coli* about 25 years ago and have since been extensively studied in this species. It is considered that all termination suppressors in *E. coli* have been identified. Recently, new suppressor tRNA genes have been synthesized in vitro and subsequently introduced into *E. coli*. Termination suppressors have also been identified in the *E. coli* bacteriophage T4 and in *Salmonella typhimurium* (Eggertson et al., 1988, Microbiological Reviews, 52, 354–374). Furthermore, termination suppressors have been identified in eucaryotic fungi including Neurospora spp., *Saccharomyces cerevisiae* and *Schizosaccharomyces pombe*.

Hitherto, nonsense or termination suppressors have not been identified in bacterial species belonging to the industrially important group of lactic acid bacteria which i.a. are commonly utilized as starter cultures in the production of a variety of food products including dairy products, meat products, vegetable products, bakery products and wine, during which production these starter cultures produce lactic acid and other organic acids and in many instances also desirable flavour-enhancing metabolites.

Furthermore, attempts by the present inventors to construct amber-suppressing strains of lactic acid bacteria by introducing cloned known suppressor genes from *E. coli* proved unsuccessful. Thus, it was attempted to introduce the *E. coli* supB gene (Thorbjarnadòttir et al., 1985), the *E. coli* supE gene (Nakajima et al., 1981) and the *E. coli* supF gene (Ryan et al., 1980). These three suppressor genes were moved to pFDi3 described in the below Example 3 and analyzed for suppressor activity in *Lactococcus lactis* by testing for the expression of erythromycin resistance. None of the three *E. coli* suppressor genes expressed suppressor activity in *Lactococcus lactis*.

In many instances it is advantageous to use lactic acid bacterial starter cultures which are composed of two or more different species, since the metabolic activity of one species may enhance the growth of an other species or because different lactic acid bacterial species may have particularly advantageous effects on flavour development of the food product at specific stages of the food production.

Accordingly, an industrial need exists to provide mixed lactic acid bacterial starter cultures in which a particular characteristic is confined (or contained) to a particular strain. Commonly, genes coding for desired characteristics of a lactic acid bacterium are located on extrachromosomal replicons such as plasmids. It may therefore be advantageous to have such replicons contained in their original host species. As used herein, the term "contained" indicates confinement of a replicon to a specific host cell or to the stable maintenance of a replicon in a lactic acid bacterial host cell when this host cell is present in a specific environment. This stable maintenance in a particular host cell of a replicon may also be referred to as stabilization of that replicon.

The term "containment" may also as used herein as encompassing the phenomenon that the growth and/or viability of a specific lactic acid bacterial strain in a particular environment is controlled.

The known methods of stably maintaining (stabilizing) replicons to a host cell involve the insertion of relatively large DNA sequences such as a partitioning function. However, as it is well-known, the insertion of large DNA sequences involves the risk of deletion of other sequences from the replicon. It has now been found that nonsense suppressor-encoding lactic acid bacterial strains may be developed which provide the means of a novel and advantageous method of confining replicons to lactic acid bacterial strains. In contradistinction to the known methods of stabilizing (confining) replicons to host cells, the method as defined herein makes use of genes coding for suppressor TRNA which are small and may be inserted without causing deletions of desired genes.

In the production of food products where live microorganisms are used, it may be critical for the obtainment of the desired quality of the products that the microbial processes can be controlled effectively. This is particularly important when mixed starter cultures as defined above and which comprise a multiplicity of strains, are used. Such a control has hitherto been difficult to achieve since specific regulating mechanisms at the level of cell numbers and activity and at the level of gene expression in particular strains had to be selected individually for each of the strains used in the mixed culture. However, the present invention has made it possible that the same suppressor gene under the control of the same regulatory mechanism may be inserted in all of the strains of the mixed starter culture whereby the activity of the species of such a culture may be regulated concomitantly or, if different regulatory sequences are inserted in individual species members of the starter culture, the activity of the individual members may be regulated independently.

SUMMARY OF THE INVENTION

Accordingly, the present invention relates in a first aspect to a method of isolating a nonsense suppressor-encoding lactic acid bacterium, comprising the steps of (i) mutagenizing a replicon capable of replicating in a lactic acid bacterium, said replicon comprising a gene encoding a selectable marker which is expressible in the lactic acid bacterium, (ii) selecting from the mutagenized replicon of (i) a replicon containing a nonsense mutation in the gene encoding the selectable marker, (iii) mutagenizing a lactic acid bacterium which does not encode a nonsense suppressor, (iv) introducing the replicon of step (ii) into said mutagenized lactic acid bacterium, and (v) selecting from the mutagenized lactic acid bacterium of (iv) a nonsense suppressor-encoding transformed lactic acid bacterium in which the selectable marker is expressed.

In another aspect there is provided a method of isolating a nonsense suppressor-encoding lactic acid bacterium, comprising the steps of (i) mutagenizing a replicon without nonsense mutations but containing a selectable marker, which plasmid is inherently capable of replicating in a lactic acid bacterium, (ii) selecting from step (i) a replicon containing a nonsense mutation rendering the replicon incapable of replicating, (iii) mutagenizing a lactic acid bacterium which does not encode a nonsense suppressor, (iv) introducing into said mutagenized lactic acid bacterium the replicon of step (ii), and (v) selecting a transformed lactic acid bacterium in which the introduced replicon is capable of replicating.

In further aspects, the present invention also relates to an isolated pure culture of a lactic acid bacterium comprising a gene coding for a nonsense suppressor, to a composition comprising such an isolated pure culture of a lactic acid bacterium as defined herein, and a carrier, and to the use of the composition as a starter culture in the preparation of a food product selected from a dairy product, a vegetable product, a meat product and a bakery product.

The invention also pertains to a plasmid comprising lactobacterial DNA and capable of replicating in a lactic acid bacterium, the plasmid comprising a gene coding for a nonsense suppressor.

In one interesting aspect, the invention relates to a method of confining an extrachromosomal replicon capable of replicating in lactic acid bacteria to a first kind of lactic acid bacterial cells, where said replicon could be naturally transferred to a second kind of lactic acid bacterial cells, which method comprises providing the first kind of lactic acid bacterial cells as cells containing a nonsense suppressor-encoding gene, the cells being transformed with the replicon in the form of a nonsense mutant hereof having lost its capability of replicating in lactic acid bacterial cells, the gene product of the nonsense suppressor-encoding gene being capable of restoring the capability of the replicon to replicate in lactic acid bacterial cells whereby, if a cell of the second kind which does not contain a nonsense suppressor gene encoding a gene product capable of restoring the capability of the nonsense mutant of the replicon to replicate in lactic acid bacteria, receives said extrachromosomal replicon, the replicon will not replicate in the second kind of lactic acid bacterial cell.

In a further interesting aspect, the present invention relates to a method of stably maintaining an extrachromosomal replicon in lactic acid bacterial host cells growing in a particular environment, comprising providing said host cells as nonsense mutant cells having lost the capability of growing in said environment, and transformed with an extrachromosomal replicon containing a nonsense suppressor gene encoding a gene product restoring the capability of the nonsense mutant cells to grow in said environment whereby, if the replicon is lost from the lactic acid bacterial cells, the cells will not grow.

In a still further aspect the present invention provides a method of controlling the number of lactic acid bacterial cells in a particular environment allowing growth of lactic acid bacteria, comprising providing the bacteria with a nonsense mutation in a gene the expression of which has an effect on the viability or the growth of the bacteria, and inserting in the bacteria a nonsense suppressor-encoding gene under the control of a regulatable promoter, the gene product of which, when expressed at one level, prevents the expression of the nonsense mutation and which, when not expressed, or expressed at a different level causes the cells to cease growth or to die.

DETAILED DISCLOSURE OF THE INVENTION

As mentioned above, the method of isolating a nonsense suppressor-encoding lactic acid bacterium comprises as an initial step the provision of a replicon capable of replicating in the lactic acid bacterium, which replicon contains a nonsense mutation in a gene coding for a selectable marker (a marker gene) and preferably also a non-mutated gene coding for a further selectable gene product. The selectable marker gene may be selected from any gene coding for a readily detectable phenotype such as a gene the expression of which confers resistance to an antibiotic to which the lactic acid bacterium is sensitive, including as examples resistance to erythromycin, chloramphenicol or tetracycline. Other useful mutant markers include auxothrophic phenotypes such as Pur⁻ chromosomal mutants or replicons such as plasmid or bacteriophage mutants having lost their inherent capability of replicating in the lactic acid bacterium.

In accordance with the present invention, any suitable conventional mutagen including ultraviolet and ionizing radiation and chemical mutagens including mutagens which affect non-replicating DNA such as $HNO_2$, $NH_2OH$; alkylating agents including as examples ethyl methane sulphonate (EMS) and N-methyl-N'-nitro-N-nitrosoguanidine (NTG); and base analogs or frameshift mutagens, may be used for mutating the marker gene. Furthermore, mutagenesis may be site-directed mutagenesis, using recombinant DNA techniques including the use of primers in the polymerase chain reaction, of transposable elements or bacterial mutator strains, e.g. the mutator strain LE30.

Although the nonsense mutation as defined above may most conveniently be provided by subjecting the replicon to a mutagenization treatment as also defined above, it is not excluded that a replicon containing a nonsense mutation in the gene coding for a selectable marker may be an isolated spontaneous mutant.

In the following, a nonsense mutation is designated by the conventional designation of the gene in which the mutation has occurred, followed by an indication of the type of nonsense mutation. Thus, a nonsense mutation recognizable by either an amber or ochre suppressor, in genes coding for erythromycin and chloramphenicol resistance, respectively is designated erm-am and cat-am, respectively.

In certain embodiments of the invention, the mutated replicon may contain two or more nonsense mutations, e.g. in genes coding for antibiotic resistance such as erm-am and cat-am. Such replicons containing multiple nonsense mutations may conveniently be constructed by recombining in one replicon DNA sequences containing the mutations. Thus, as one example which is described in details in the following, a starting plasmid may be isolated which contains a nonsense mutation in the erm gene. In a subsequent. step, a DNA sequence comprising this gene may be inserted in an other plasmid carrying a nonsense mutation in the cat gene. A typical example of such a replicon containing two nonsense mutations is the plasmid pFDi10 as described below.

When an isolated nonsense replicon mutant is obtained, it is used as a means of isolating a lactic acid bacterium in which a nonsense suppressor mutation has been generated by subjecting a population of a parent lactic acid bacterium which does not encode a suppressor mutant, to a treatment with a mutagen as defined above. The mutant replicon is introduced by means of conventional transformation techniques into a population of the thus mutagenized lactic acid bacterial cells and a nonsense suppressor mutant cell is selected from these transformed cells by growing the cells under conditions allowing the replicon marker gene to be expressed and isolating host cells in which the nonsense mutation in the replicon is expressed. When e.g. the mutation in the replicon is in a gene conferring resistance to one or more antibiotics, a nonsense suppressor-encoding mutant of the transformed lactic acid bacterial cells may conveniently be selected from a medium containing this/these antibiotic(s).

That a transformed cell capable of growing in such a selective medium is a true suppressor-encoding cell may subsequently be verified by (i) transforming the same nonsense mutation-containing replicon to known suppressor host cells in which the replicon can replicate and to corresponding host cells without the suppressor gene and (ii) reintroducing the replicon into the assumed suppressor-encoding cell to confirm the suppressor phenotype.

The thus obtained nonsense-suppressing transformants may subsequently be cured of the replicon e.g. by growing the transformants in a non-selective medium or by treating them with a conventional plasmid curing agent.

The suppressor gene may be located on the chromosome or on an extrachromosomal replicon.

Most mutations in a tRNA-encoding gene leading to the formation of a nonsense suppressor are located in the anticodon triplet and alter it to CUA, UUA or UCA. Such suppressors may be referred to as amber, ochre and opal suppressors, respectively. Following the rules of nomenclature of Demerec et al. (Genetics, 1966, 54, 61–76) which was suggested for termination (nonsense) suppressors in $E. coli$ the symbol "sup" and assigned capital letters as gene designations, e.g. supB, supC or supZ, are used herein also to designate suppressor genes in lactic acid bacteria. In this system, the term $sup^+$ (e.g. $supB^+$) represents the wild-type allele and $sup^-$ (e.g. $supB^-$) represents the mutant allele.

Amber suppressors generally recognize only amber codons whereas all ochre suppressors will recognize amber as well as ochre nonsense codons. The spectrum of suppression of a nonsense mutation depends not only on the anticodon (amber or ochre), but also on the amino acid inserted at the nonsense codon. When the suppressor tRNA is causing the insertion of an amino acid which is different from the wildtype protein, the resulting protein may be non-functional. Some nonsense mutations may therefore only be suppressed by one type of suppressors whereas others may be suppressed by several or all suppressors.

Suppressors may show a poor efficiency of suppression which means that the termination of translation at the nonsense codon is not completely suppressed. Thus, a suppressor with an efficiency of 10% will allow only 10% of the protein encoded by a gene with a nonsense mutation to be synthesized in full length whereas 90% of the protein molecules will terminate at the nonsense codon. Most ochre suppressors are only 5% to 10% efficient whilst amber suppressors typically have efficiencies in the range of 25% to 65%.

As it has been mentioned above, the present invention relates in one aspect to a method of isolating a nonsense-suppressor-encoding lactic acid bacterium in which the replicon being mutagenized to obtain the nonsense mutation is one, which prior to the mutagenesis is capable of replicating in the lactic acid bacterium and which has acquired a nonsense mutation in one or more genes, whereby the isolated mutated replicon is no longer capable of replication in the lactic acid bacterium not containing a suppressor gene, the product of which may suppress the replication nonsense mutation.

Such nonsense mutated replicons having lost their capability of replication may be derived from plasmids or bacteriophages normally replicating in lactic acid bacteria. As one example which is also described in details in the below example 4A, the citrate plasmid of $Lactococcus\ lactis$ subsp. $lactis$ biovar $diacetylactis$ strain DB1138 may be mutagenized e.g. by means of the polymerase chain reaction to obtain an amber nonsense mutation in the repB gene. The replicon from which a non-replicating nonsense mutant may be derived may also be a bacteriophage including as an example the prolate Lactococcus phage φMPC100 from which mutants with nonsense mutations in genes essential for phage development may be derived. Such mutants have lost the capability of the parent phage to form plaques on sensitive lactic acid bacteria.

Nonsense mutants of bacteriophages may e.g. suitably be generated by mutagenization with hydroxylamine ($NH_2OH$).

As also mentioned above, there is provided herein an isolated pure culture of a lactic acid bacterium comprising a gene coding for a nonsense suppressor such as a gene coding for amber, ochre or opal suppressor tRNA. Such a gene coding for a termination (nonsense) suppressor may be located on the chromosome of the bacterium or it may in other embodiments be located extrachromosomally e.g. on a plasmid or it may be incorporated in the cell as a prophage.

When the lactic acid bacterium of the above culture is one used as a starter culture in food production, it may be preferred that the bacterium only contains DNA of lactic acid bacterial origin including DNA isolated from plasmids or other replicons having the lactic acid bacterium as their natural host organism. Accordingly, the nonsense suppressor-containing lactic acid bacterium may in preferred embodiments contain a suppressor gene which is a native gene or which is derived from a heterologous lactic acid bacterium. In the art, recombinant lactic acid bacteria which only contain DNA of lactic acid bacterial origin are also referred to as "food grade" organisms since it is generally considered that the use of such organisms may be allowable by relevant governmental authorities for use in food manufacturing.

As it will be understood from the above, the suppressor gene carried by the pure culture may be an inserted gene either derived from a heterologous lactic acid bacterial strain or from a heterologous lactic acid bacterial plasmid or it may be a suppressor gene derived from the mutagenization of a native, homologous gene which may either be chromosomally or extrachromosomally located. When the gene is an inserted gene, it may be inserted in the chromosome or it may be introduced on a plasmid or a bacteriophage.

In useful embodiments of the invention, the lactic acid bacterial cells of the pure culture may, in addition to the suppressor gene, further comprise a nonsense mutation which is suppressible by the nonsense suppressor. When present in the same cells, the suppressor gene and the gene with the nonsense mutation may preferably be located on different replicons, e.g. so that the suppressor gene is located on the chromosome whereas the nonsense mutation occur in a gene carried by an extrachromosomal replicon. In other useful embodiments, the location of the two genes is the reverse.

In certain preferred embodiments, the suppressor encoded by the lactic acid bacterium constituting the isolated pure culture is an amber suppressor. The suppressor may e.g. be one suppressing a nonsense mutation which, in the absence of a nonsense suppressor capable of suppressing the mutation, confers auxotrophy such as a nonsense mutation in a gene involved in the synthesis of purine nucleotides from their precursors. Thus the culture may comprise a lactic acid bacterium which is a nonsense pur mutant.

Accordingly, in one particularly useful embodiment the lactic acid bacterium in a culture is a strain which contains a nonsense mutation which is suppressed by a suppressor gene located on a food grade plasmid as described above. As an example such a plasmid may be constructed so as to contain a replication region of a lactic acid bacterium or a plasmid naturally occurring in such a bacterium, e.g. the replication region of a plasmid naturally harboured by a Lactococcus sp. including the replication region of the citrate plasmid in *Lactococcus lactis* subsp. *lactis* biovar *diacetylactis* and a suppressor gene from a lactic acid bacterium as defined herein such as e.g. a suppressor tRNA gene of *Lactococcus lactis* strain FD100 as described hereinbelow. In such a plasmid the suppressor gene will function as a selectable marker if the nonsense mutation is one which in the absence of a corresponding suppressor gene will render the bacterium incapable of growing in a particular environment, such as milk or any other food product or agricultural product where lactic acid bacteria are used.

A plasmid construct as described above will be useful as a cloning vector if further provided with one or more suitable unique restriction sites comprising DNA isolated from a lactic bacterium or is a non-coding synthetic linker/polylinker sequence. Such a cloning vector is encompassed by the present invention.

Preferably such food grade cloning vectors have a size allowing for the insertion of desirable genes. Accordingly, a suitably sized cloning vector as defined herein has a size which is in the range of 0.5 to 20 kb, although larger vectors may also be used. In preferred embodiments the cloning vector has a size in the range of 1 to 10 kb, such as in the range of 2 to 5 kb. Examples of such cloning vectors are the pFG plasmids as described below.

In accordance with the invention such cloning vectors may be used for insertion of genes coding for desirable gene products, in particular genes isolated from lactic acid bacteria. Such useful genes include genes coding for enzymes which has an advantageous effect on the quality of a food product the manufacturing or preservation of which includes the addition of viable lactic acid bacterial cultures as it has been described above. Thus, such genes inserted into the above cloning vector may code for peptidases, including a dipeptidase, examples of such peptidases being the gene products of the genes pepN, pepc and pepR as exemplified below. Other interesting gene products include lipases, proteases, nucleases and enzymes which are involved in the carbohydrate metabolism of the host bacterium. Inserted genes may also be prokaryotic genes isolated from non-lactic acid bacterial species.

It is furthermore contemplated the useful genes in the present context are eucaryotic genes e.g. mammalian genes coding for immunologically, enzymatically or pharmacologically active gene products, including as an example proteolytic enzymes such as chymosin or plasminogen.

It has been found that a lactic acid bacterium normally coding for a particular enzyme may have the expression of this enzyme increased by a factor of at least 2 such as at least 5 or even by a factor of at least 10 by being transformed with a cloning vector as defined above, in which a gene coding for an enzyme having similar activity, is inserted. Examples of such vectors are the plasmid pFG1 derivatives pFG2, pFG3, pFG4, pFG5 and pFG6 as described in the below examples.

It has been found that the gene product of the suppressor gene of the above food grade vector may in some instances be "overexpressed" to an extent where the normal growth of the host cell may be impaired. However, it has also been found that mutants may occur in which the natural promoter for the suppressor gene of the vector is mutated, resulting in a decreased suppressor gene expression allowing the host cell to grow normally. In accordance herewith the invention provides in one embodiment a cloning vector comprising a suppressor gene with a promoter functionally linked thereto in which a mutation occur. It has also been discovered that mutations may occur in a nonsense mutation-containing lactic acid bacterial host cell chromosome which enables the cell when hosting a vector plasmid from which a suppressor gene is overexpressed, to grow normally. Such host cells which apparently are refractory to the effect of the suppressor gene "overproduction" may be very useful hosts for cloning vectors such as e.g. the above pFG1 plasmids and its derivatives.

The lactic acid bacterial culture may comprise any lactic acid bacterium. As used herein, the term "lactic acid bacterium" designates a group of bacteria having as a common characteristic the capability to produce lactic acid from sugars. The majority of the species belonging to this group can be characterized as gram-positive, catalase negative, microaerophilic or anaerobic bacteria which may be cocci or rods. The anaerobic genus Bifidobacterium is also generally included in the group of lactic acid bacteria. Accordingly, the pure culture of a lactic acid bacterium preferably comprises bacteria selected from Lactococcus spp., Streptococcus spp., Lactobacillus spp., Leuconostoc spp., Pediococcus spp. and Bifidobacterium spp. In certain useful embodiments, the lactic acid bacterium in the isolated culture is *Lactococcus lactis*.

The culture may, in accordance with the invention, comprise two or more different species of lactic acid bacteria or two or more strains of the same species. As mentioned above, it is common in the production of food products, where lactic acid bacterial starter cultures are used, to apply mixed cultures, i.e. cultures comprising a multiplicity of strains. As an example hereof it can be mentioned that a mixed culture of *Lactobacillus bulgaricus* and *Streptococcus thermophilus* is typically used in the production of yoghurt. In other dairy products a mixed culture of *Bifidobacterium bifidum* and *Lactobacillus acidophilus* may be used.

In addition to their use as food starter cultures, lactic acid bacteria according to the present invention may also be applied in the production of animal feed such as silage where starter cultures are inoculated in the feed crop to be ensiled in order to obtain a preservation hereof, or in protein rich animal waste products such as slaughtering offal and fish offal, also with the aims of preserving this offal for animal feeding purposes. Yet another significant application of lactic acid bacterial cultures according to the present invention is the use of such cultures as so-called probiotics. By the term "probiotic" is in the present context understood a microbial culture which, when ingested in the form of viable cells by humans or animals, confers an improved health condition, e.g. by suppressing harmful microorganisms in the gastrointestinal tract, by enhancing the immune system or by contributing to the digestion of nutrients.

The culture as defined above may advantageously be in a concentrated form containing e.g. at least $10^9$ colony forming units per g of the culture. Such concentrates may be provided as a cell slurry e.g. separated from a fermenter or as a frozen or freeze-dried culture.

In an interesting embodiment, the culture according to the invention comprises a lactic acid bacterium wherein the gene coding for a nonsense suppressor is under the control of a regulatable promoter. As used herein, the term "regulatable promoter" is used to describe a promoter sequence possibly including regulatory sequences for the promoter which promoter is regulatable by one or more factors selected from the pH and/or the arginine content of the medium, the growth temperature, a temperature shift eliciting the expression of heat shock genes, the composition of the growth medium including the ionic strength/NaCl content and the growth phase/growth rate of the lactic acid bacterium. Such a regulatable promoter may be the native promoter or it may be an inserted promoter not naturally related to the suppressor gene either isolated from the lactic acid bacterium itself or it may be a heterologous promoter sequence.

A promoter sequence as defined above may comprise further sequences whereby the promoter becomes regulated by a stochastic event. Such a regulation may e.g. be useful in lactic acid bacterial cultures for which it may be advantageous to have a gradually decreasing activity of the suppressor gene under control of the promoter sequence. Such further sequences may e.g. be sequences, the presence of which results in a recombinational excision of the promoter or of genes coding for substances which are positively needed for the promoter function.

As mentioned above, the invention relates in further aspects to a composition comprising an isolated pure culture of a lactic acid bacterium as defined above, and a microbiologically acceptable carrier and to the use of such a composition as a starter culture in the preparation of a food product. It may be preferred that such a composition contains at least $10^9$ colony forming units of the bacterium. Preferably, the carrier may comprise nutrients such as an assimilable carbohydrate or a nitrogen source, which can be utilized readily by the lactic acid bacterium. Typically, such a composition is provided in the form of a frozen or freeze-dried composition.

As mentioned above, the invention pertains in a further aspect to a plasmid comprising a gene coding for a nonsense suppressor. The gene may in certain preferred embodiments be derived from the chromosome of a lactic acid bacterium. In accordance with the present invention, the plasmid is constructed by inserting an isolated DNA sequence comprising a suppressor gene which is functional in a lactic acid bacterium, into a starting plasmid capable of replicating in a lactic acid bacterium. The starting plasmid may be one which contains a nonsense mutation, e.g. in a gene the native gene product of which is required for replication of the plasmid or in a gene conferring antibiotic resistance.

The above DNA sequence comprising a suppressor gene is preferably a small sequence such as a sequence in the range of 0.05 to 10 kb, more preferably in the range of 0.1 to 5.1 kb, such as e.g. 3.2, 1.1 or 0.25 kb. The suppressor gene may preferably encode a tRNA with an anticodon recognizing only amber codons, i.e. an amber suppressor. As an example, the DNA sequence coding for such a tRNA may be the following (SEQ ID NO:1):

1 GGAGCCATGG CAGAGTGGTA ATGCAACGGA CTCTAAATCC GTCGAACCGT

51 GTAAAGCGGC GCAGGGGTTC AAATCCCCTT GACTCCTTA

The plasmid according to the invention may further comprise an inserted gene coding for a desired gene product. In this context, interesting desired gene products include hydrolytic enzymes selected from proteases such as chymosin, peptidases including endopeptidases, lipases, nucleases and carbohydrases; lytic enzymes such as lysozyme or phage lysins; flavour enhancing substances; bacteriocins including nisin, pediocin, and bavaracin; amino acids; organic acids and pharmacologically active substances.

In accordance with the invention, the gene coding for the suppressor which is carried by the plasmid may be under the control of a regulatable promoter as defined above.

As it has been described above, it may be advantageous to confine an extrachromosomal replicon to a particular type of lactic acid bacteria and accordingly, the invention provides in one aspect a method as defined above of confining an extrachromosomal replicon to a first kind of lactic acid bacterial cells, where the replicon could be naturally transferred to a second kind of lactic acid bacterial cells. The first kind of lactic acid bacteria is preferably selected from Lactococcus spp. including *Lactococcus lactis, Streptococcus* spp., Lactobacillus spp., Leuconostoc spp., Pediococcus spp. and Bifidobacterium spp. As used herein, the term "confine" indicates that the replicon is stabilized or contained in the first kind of cells.

Nonsense mutated replicons having lost their capability of replication may be derived from plasmids or bacteriophages naturally replicating in lactic acid bacteria. One example of such a non-replicating replicon is a nonsense mutant of the citrate plasmid of *Lactococcus lactis* subsp. *lactis* biovar *diacetylactis* strain DB1138 as described above.

In accordance with the present method, the suppressor-encoding gene may be located on the chromosome or it may be a gene on a replicon such as a plasmid or a bacteriophage which is different from the one to be confined to the first kind of cells.

The replicon to be confined may in preferred embodiments be a recombinant replicon comprising a gene coding for a desired gene product as defined above.

In addition to confining a replicon as it is defined above, it may also be interesting to confine the expression of a desired gene product to a particular kind of lactic acid bacteria by a method where the gene coding for the desired gene product has a nonsense mutation causing the gene product not to be expressed. As long as such a replicon is present in a lactic acid bacterial host cell comprising a suppressor gene coding for a product capable of restoring the capability of the nonsense mutated gene to be expressed normally, the gene is expressed. However, if the replicon comprising the gene coding for the desired gene product escapes from the primary host cell to a second kind of lactic acid bacteria not having a suppressor gene as defined above, then the gene product will not be expressed in that second kind of cells.

The method of confining a replicon as defined herein is particularly interesting where a mixed culture composition of two or more strains of lactic acid bacteria between which a replicon coding for a desired gene product may be freely transferable, is used e.g. in the production of a food product as defined above. Thus, the expression of a certain gene product can be confined to one lactic acid bacterial strain in the mixed culture comprising a multiplicity of strains.

In accordance with the present invention there is also in a further useful embodiment provided a method as defined above of stably maintaining an extrachromosomal replicon, including a plasmid and a bacteriophage, in lactic acid bacterial host cells in a particular environment. In suitable embodiments of the invention, the lactic acid bacterial host cells harbouring the replicon to be stably maintained have a nonsense mutation in one or more genes conferring auxotrophy to the cells whereby the cells have lost their capability to grow in the particular environment due to a lack herein of an essential nutritive substance which cannot be synthesized by the nonsense mutant cells.

As one example, the nonsense mutation may be one which causes the host cells to lose the capability to grow in a medium which does not contain the precursors for the synthesis in the cells of purine nucleotides. Such auxotrophic mutants are also referred to as Pur⁻ mutants. Milk is such a medium not containing nucleotide precursors in amounts sufficient for growth of such Pur⁻ mutants. Accordingly, the nonsense mutant Pur⁻ lactic acid bacterial host cells will not be able to grow in milk if the replicon to be maintained is lost from the cells. Accordingly, the suppressor gene of the extrachromosomal replicon functions as a selective marker for the lactic acid bacterial host cells. In the present context, the term "a selective marker" is used to designate a genotype which renders lactic acid bacterial cells unable to grow if the replicon to be maintained is lost from the cells.

It is contemplated that auxotrophic nonsense mutants may, in accordance with the present invention be isolated, which allow an extrachromosomal replicon to be stably maintained in a lactic acid bacterium growing in other specific environments including vegetable products, meat products, bakery products, wines, fruit juices, the gastrointestinal tract, feed crops or offal to be ensiled by a lactic acid bacterium.

It is another interesting aspect of the present invention that it provides a method as defined above of controlling the number of lactic acid bacterial cells in a particular environment allowing growth of lactic acid bacteria. The regulation of the regulatable promoter can be provided as already defined herein.

In one specific embodiment of the above method, the suppressor-encoding gene is regulated so that the expression of the gene is increased causing the lactic acid bacterial cells to grow more slowly or to cease growth, or to die. Such an effect may e.g. be observed where the nonsense mutation is located in a gene coding for a gene product inhibiting the cell growth. As an example of a gene product having an inhibitory effect on growth of lactic acid bacteria may be mentioned a bacteriostatic antibiotic or bacteriocin. The gene product may also be a product such as a lytic enzyme including lysozyme and phage lysins, which is expressible in the bacterium to be controlled, in amounts which inhibits cell growth or causes the cells to die.

In another specific embodiment of the present method of controlling the number of lactic acid bacteria, the nonsense suppressor-encoding gene is regulated so that the expression of the gene is decreased or stopped. As one example hereof the lactic acid bacteria to be controlled are bacteria containing a lysogenic phage and having the nonsense mutation located in a gene selected from a gene coding for a gene product inhibiting the entering of the phage into its lytic cycle whereby, when the expression of the gene coding for the nonsense suppressor is decreased or stopped, the phage enters the lytic cycle, causing the lactic acid bacteria to die. In a further example the bacteria contains a nonsense mutation which is located in a gene coding for a gene product such as a gene involved in the nucleotide synthesis, the expression of which is required for growth of the bacteria, whereby, when the expression of the gene coding for the nonsense suppressor, is decreased or stopped, the gene product which is required for growth of the bacteria is no longer expressed, causing growth of the lactic acid bacterial cells to cease.

LEGENDS TO FIGURES

FIG. 1 illustrates the construction of plasmid pFDi10. Filled-in segments indicate DNA from pCI372 or pCI3340, open segments DNA from pVA891 and hatched segments DNA isolated from pCI160; Hi: HindIII, E: EcoRI, N: NcoI, C: ClaI, X: XbaI, B: BamHIII, P: PvuII, S: StuI.

Figure 2:
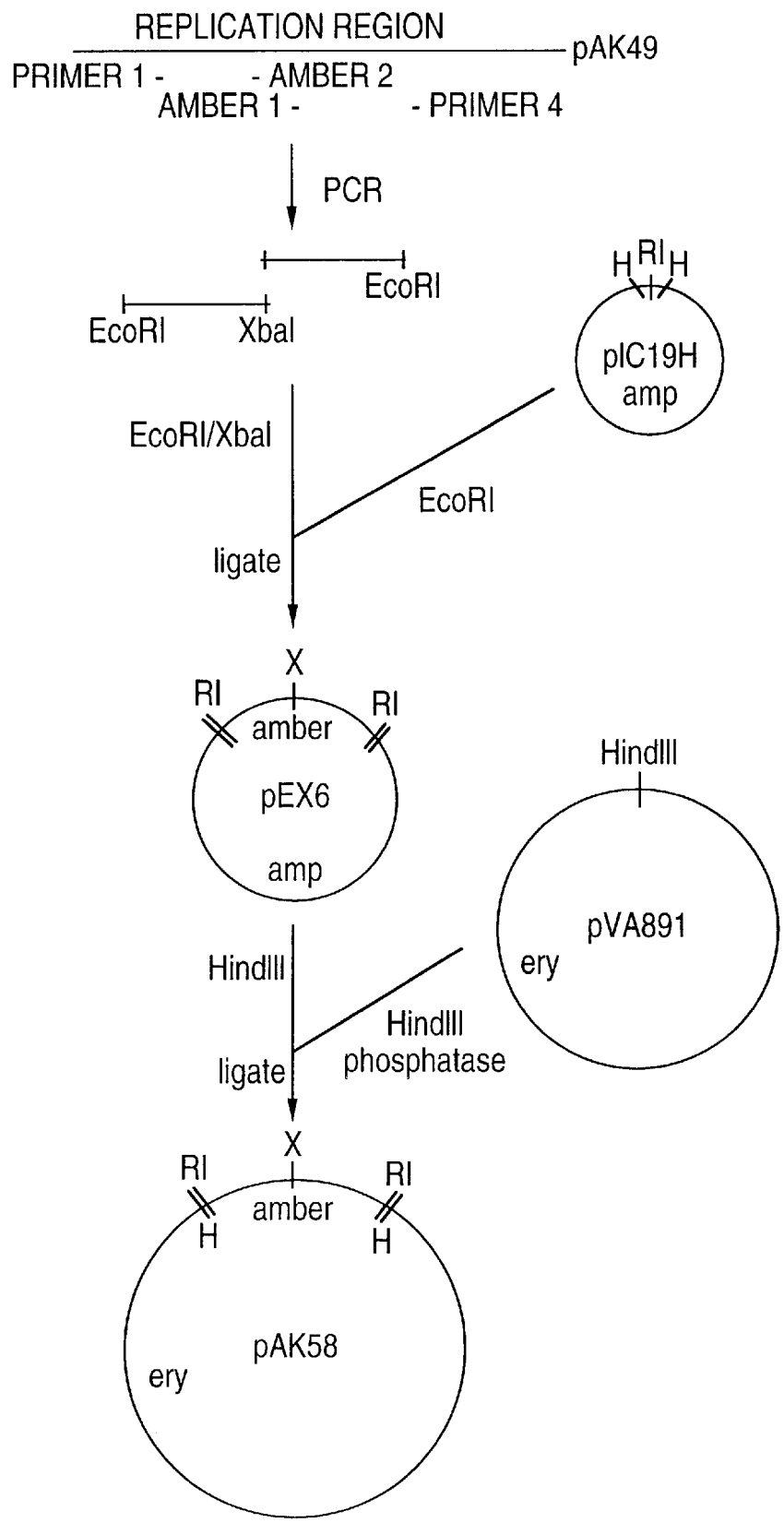
Figure 6:
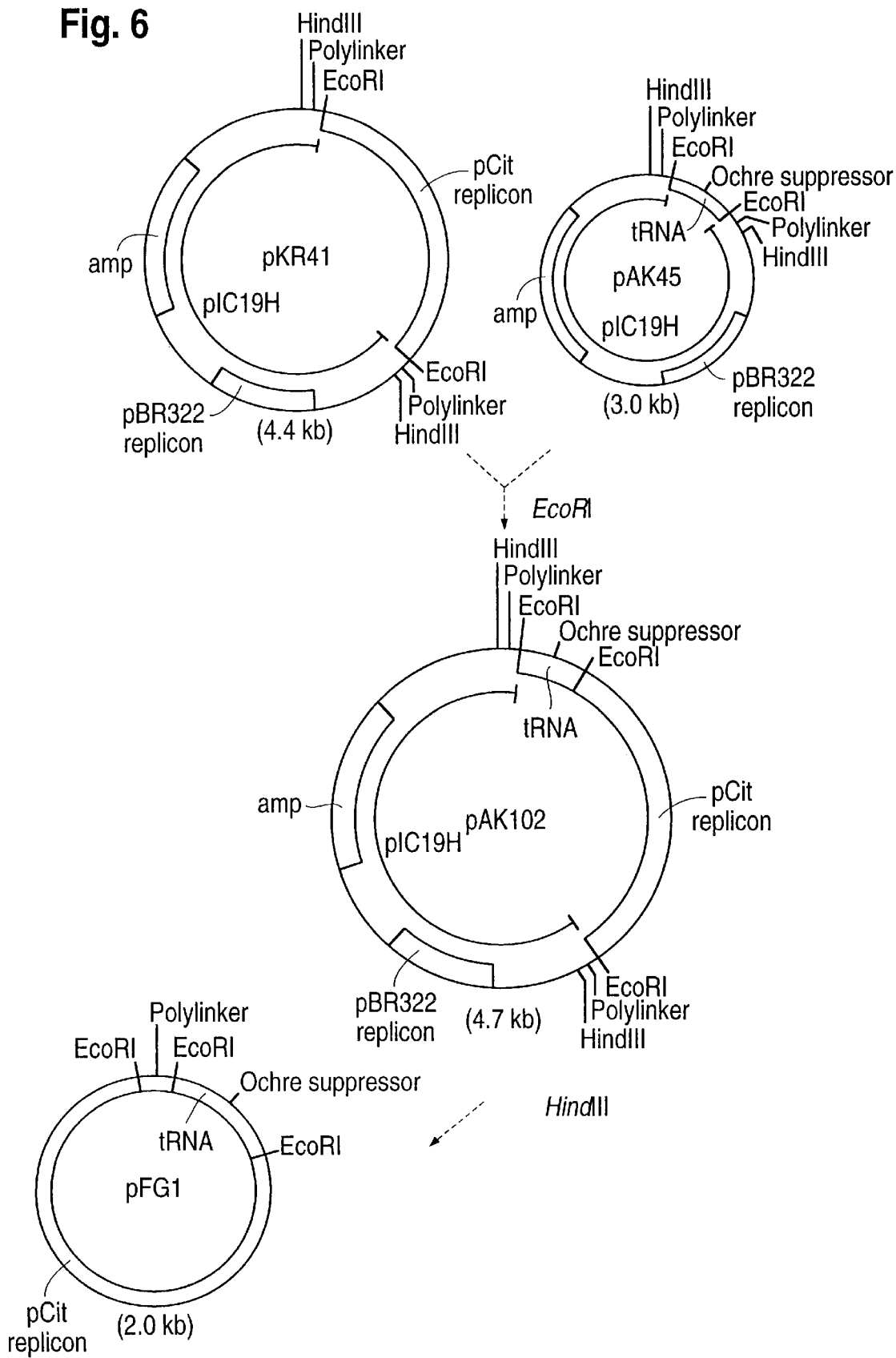

FIG. 2 illustrates the construction of plasmid pAK58;

FIG. 3 shows a 300 bp DNA sequence (SEQ ID NO:10) comprising an ochre suppressor gene isolated from the suppressor mutant strain FD100. The potential promoters are indicated with *, marking possible −35 regions and #, marking possible −10 regions. The arrows indicate an inverted repeat forming part of a potential transcription terminator. The underlined bases are expected to be transcribed and modified post-transcriptionally, e.g. by addition of CCA to the 3' end, to form an active tRNA. The start of Lactococcus DNA in the plasmids pFDi17 (nucleotide 121), pFDi18 (nucleotide 121) and pFDi19 (nucleotide 132) is indicated, FIG. 4 shows a 300 bp DNA sequence (SEQ ID NO:11) comprising an amber suppressor gene isolated from the suppressor mutant strain NJ1. The potential promoters are indicated with *, marking possible −35 regions and #, marking possible −10 regions. The arrows indicate an inverted repeat forming part of a potential transcription terminator. The underlined bases are expected to be transcribed and modified post-transcriptionally, e.g. by the addition of CCA to the 3' end, to form an active tRNA, FIG. 5 (A and B) shows the alignment of the FD100 suppressor gene (SEQ ID NO:32) (bottom line) with 20 tRNA-gln genes (SEQ ID NO:12 to SEQ ID NO:31), and FIG. 6 illustrates the construction of pFG1.

Figure 7:
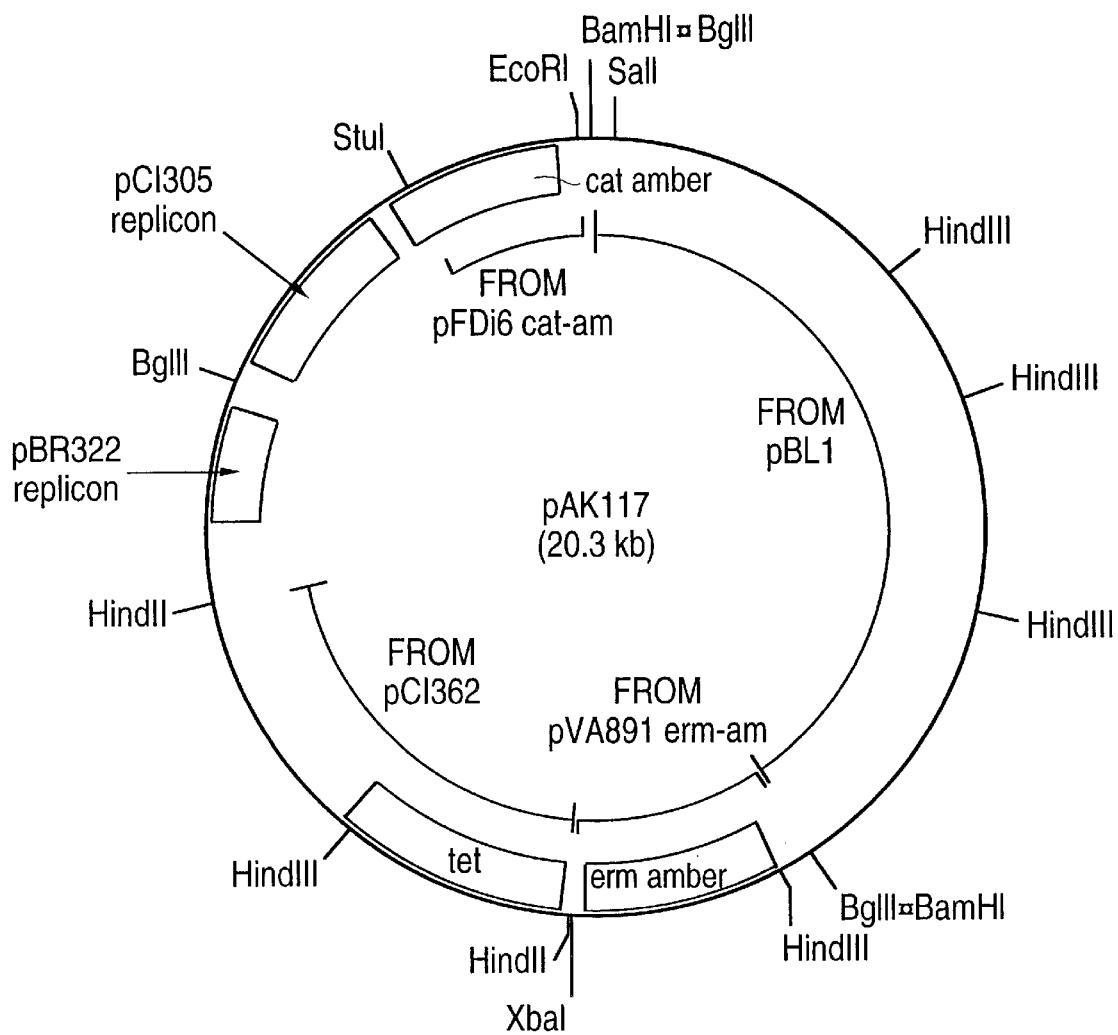

FIG. 7 illustrates the construction of pAK117.

EXAMPLE 1

The construction of a shuttle plasmid (pFDi10) carrying nonsense mutations in two antibiotic resistance genes The plasmid pFDi10 was constructed through several steps of selections and clonings. The plasmids involved in these steps are listed in Table 1 and the strains used are listed in Table 2. The individual steps are illustrated in FIG. 1 and described in detail below.

In the following, the nonsense mutations in the erm and cat genes are designated erm-am and cat-am solely to indicate that the mutations are suppressed by amber suppressors in *E. coli*. No other attempts were made to analyze the type of the nonsense mutations.

TABLE 1

Plasmids uses for the construction of pFDi10

| Plasmid | Host | Antibiotic resistance genes | Reference |
|---|---|---|---|
| pVA891 | *E. coli* | cat, erm | Macrina et al. 1983 |
| pCI160 | *E. coli* | tet, bla | Hill et al. 1988 |
| pCI372 | *E. coli*/*L. lactis* | cat | Hayes et al. 1990 |
| pCI3340 | *E. coli*/*L. lactis* | cat | Hayes et al. 1990 |
| pVA89erm-am | *E. coli* | cat, erm-am | This work |
| pFDi6 | *E. coli*/*L. lactis* | cat, erm | This work |
| pFDi6cat-am | *E. coli*/*L. lactis* | cat-am, erm | This work |
| pFDi81 | *E. coli*/*L. lactis* | cat, tet | This work |
| pFDi9 | *E. coli*/*L. lactis* | cat-am, tet | This work |
| pFDi10 | *E. coli*/*L. lactis* | cat-am, erm-am, tet | This work |

TABLE 2

Strains used in the construction of pFDi10

| Strain | Species | Relevant genotype | Reference |
|---|---|---|---|
| MG1363 | *Lactococcus lactis* | | Gasson 1983 |
| LE30 | *E. coli* K12 | mutD | Silhavy et al 1984 |
| R594 | *E. coli* K12 | sup° | Campbell 1965 |
| BR2024 | *E. coli* K12 | sup° | Austin et al. 1983 |
| BR2025 | *E. coli* K12 | supD | Austin et al. 1983 |
| BR2026 | *E. coli* K12 | supE | Austin et al. 1983 |
| BR2027 | *E. coli* K12 | supF | Austin et al. 1983 |

1. The construction of pVA891erm-am

The mutator strain LE30 was used to mutagenize pVA891. Competent cells of LE30 were prepared by inoculating LE30 into AB minimal medium (Clark & Maaløe 1967) and allowing growth at 37° C. to continue until the $OD_{600}$ was 0.4. The cells were harvested by centrifugation and made competent and subsequently transformed with pVA891 as described by Sambrook et al., 1989. Transformants were selected by plating on LB agar plates supplemented with 10 μg/ml chloramphenicol. Cells from plates containing a total of more than 1000 colonies were pooled by adding 2 ml of LB-broth per plate and resuspending the cells using a bent glass rod. The cells from the suspension were harvested by centrifugation and the plasmids extracted as described in Sambrook et al., 1989. This plasmid preparation was the mutagenized plasmid stock of pVA891.

Strain R594 was transformed with the mutagenized stock of pVA891 and $Cm^R$ transformants selected on LB supplemented with 10 μg/ml chloramphenicol. More than $5 \times 10^3$ colonies were pooled as described above, and this mixed culture was enriched for erythromycin sensitive mutants by a procedure similar to the enrichment for auxothrophic mutants described by Miller 1972. The enrichment was done by inoculating the mixed culture into 250 ml LB supplemented with 250 μg/ml erythromycin to an $OD_{600}$ of 0.02. After 2 hours incubation at 37° C. the OD had increased to 0.1. At this point of time ampicillin was added to a concentration of 50 μg/ml. The culture was incubated further at 37° C. for 2 hours. At this time the $OD_{600}$ had decreased to 0.04. The cells were harvested by centrifugation and washed in AB minimal medium and finally resuspended in AB minimal medium. Dilutions of the resuspended cells were plated on LB+10 μg/ml chloramphenicol. 300 chloramphenicol resistant colonies were screened for erythromycin sensitivity by streaking on LB+250 μg/ml erythromycin. Out of the 300 colonies tested, 113 were found to be erythromycin sensitive. From these 113 mutants individual overnight cultures were prepared in LB+10 μg/ml chloramphenicol. A pool containing 50 μl of each culture was used for the preparation of plasmids.

This plasmid pool was transformed into BR2024, BR2025 and BR2026, respectively. The transformed cells were plated on LB +10 μg/ml chloramphenicol and on LB+250 μg/ml erythromycin. Chloramphenicol resistant transformants were obtained with all three strains whereas erythromycin resistant transformants were only obtained with strain BR2026. An erythromycin resistant transformant of BR2026 was purified by streaking to single colonies twice. From this transformant the plasmid pVA891erm-am was isolated.

To verify the presence of an amber mutation, the purified pVA891erm-am plasmid was transformed into BR2024, BR2025 and BR2026, respectively and transformants were selected on LB+250 μg/ml erythromycin and on LB+10 μg/ml chloramphenicol. The numbers of transformants obtained are listed in table 3. The result shows that pVA891erm-am indeed carries a mutation in the erm gene which can be suppressed efficiently by the supE amber suppressor and with lesser efficiency by the supD amber suppressor.

TABLE 3

Number of transformants with suppressed pVA891erm-am

| | STRAINS | | | | | |
|---|---|---|---|---|---|---|
| | BR2024 sup° | | BR2025 supD | | BR2026 supE | |
| | $cm^R ery^R$ | $ery^R/cm^R$ | $cm^R ery^R$ | $ery^R/cm^R$ | $cm^R ery^R$ | $ery^R/cm^R$ |
| Not transformed with DNA | 2 | 9 | 2 | 4 | 0 | 1 |
| pVA-891-erm-am | 600 | 4 | $1.5 \times 6^{-2}$ | 255 | 70 | 0.3 | 400 | 400 | 1 |

2. The construction of pFDi6 pFDi6 is a plasmid capable of replicating in *E. coli* as well as in *Lactococcus lactis*. pFDi6 carries two antibiotic resistance markers (cat and erm). These two markers are expressed well in both hosts.

pDFi6 was constructed by inserting the erm gene of pVA891 into the shuttle plasmid pCI3340. This was done by digesting 1 μg of pVA891 DNA simultaneously with the restriction enzymes HindIII, ClaI and PvuII (PvuII was included to increase the frequency of the desired event, as PvuII does not cleave the fragment carrying the erm gene). 1 μg of pCI3340 was digested with the restriction enzymes HindIII and ClaI. The digested plasmids were mixed, ligated and transformed into R594 as described in Sambrook et al., 1989. Transformants were selected on LB+10 μg/ml chloramphenicol. 222 chloramphenicol resistant colonies were screened for erythromycin resistance and 24 were found to be resistant to both antibiotics. Plasmid DNA was extracted from 10 of these and all 10 were found to have identical size and structure. One of these was kept as pFDi6.

3. The construction of pFDi6cat-am

A derivative of pFDi6 carrying a nonsense mutation in the cat gene was constructed by a method analogous to that used in the construction of pVA891erm-am.

pFDi6 was transformed into the mutator strain LE30 and transformants selected on LB+250 μg/ml erythromycin. More than $10^3$ colonies were pooled and plasmid DNA extracted. This stock of mutated pFDi6 DNA was transformed into R594 and transformants selected on LB+250 μg/ml erythromycin. More than $10^3$ transformants were pooled and used to inoculate 250 ml LB+10 μg/ml chloramphenicol to an $OD_{600}$ of 0.03. After growth at 37° C. for 2½ hours the $OD_{600}$ had increased to 0.360. At this time ampicillin was added to a final concentration of 50 μg/ml and incubation continued for an additional 2 hours. At this time the $OD_{600}$ had decreased to 0.09, and the cells were harvested by centrifugation, washed in AB minimal medium, resuspended in AB minimal medium and dilutions were plated on LB+250 μg/ml erythromycin. 500 erythromycin resistant colonies were screened for chloramphenicol sensitivity and 44 were found to be chloramphenicol sensitive. An overnight culture of each of these 44 mutants was prepared in LB+250 μg/ml erythromycin. Plasmid DNA was extracted from a mixture of all 44 cultures. This mixture of mutated plasmids was transformed into BR2024, BR2025, BR2026 and BR2027, respectively.

Erythromycin resistant transformants were obtained with all four strains whereas chloramphenicol resistant transformants could only be obtained in BR2025, BR2026 and BR2027. One of the chloramphenicol resistant transformants of BR2025 was purified and the plasmid extracted from this transformant was shown to carry pFDi6cat-am by repeating the transformation into BR2024, BR2025, BR2026 and BR2027, respectively. The amber mutation in pFDi6cat-am is suppressed by supD, supE and supF.

4. The construction of pFDi81

The tetracycline resistance gene of pCI160 was chosen for the construction of pFDi81 and subsequently of pFDi9 and pFDi10, as this tetracycline resistance gene is well expressed in Lactococcus spp (Hill et al. 1988).

1 μg of each of the plasmids pCI160 and pCI372 were digested with HindII. The digests were mixed, ligated and transformed into competent cells of R594 as described in Sambrook et al. 1989. Transformants were selected by plating on LB agar supplemented with 10 μg/ml chloramphenicol. 200 colonies were screened for tetracycline resistance by streaking on LB agar supplemented with 10 μg/ml tetracycline. 8 colonies were found to carry plasmids with the tetracycline resistance gene inserted in pC1372. One of these was kept and the plasmid designated pFDi81.

5. The construction of pFDi9 pFDi9 is a plasmid of the same structure as pFDi81, but carrying the cat-am gene instead of the wildtype cat gene. The EcoRI-StuI fragment of pFDi81 carrying the cat gene was substituted with the EcoRI-StuI fragment of pFDi6cat-am to construct pFDi9. 1 μg of pFDi8l DNA was digested with EcoRI, StuI and NcoI (NcoI was included to reduce the frequency of clones carrying the wildtype cat gene). 1 μg of pFDi6cat-am was cleaved with StuI+EcoRI. The two digests were ligated and transformed into BR2026 (supE). Transformants were selected on LB agar supplemented with 10 μg/ml chloramphenicol and 10 μg/ml tetracycline.

More than 500 transformants were obtained. Three colonies were purified and plasmid DNA extracted. Transformation into R594 and BR2026, respectively showed that all three plasmids carried the cat-am gene as chloramphenicol resistant transformants could be obtained in the supE strain BR2026 and not in the non-suppressing strain R594. Tetracycline resistant transformants were obtained with both strains. One of the three plasmids was kept as pFDi9.

6. The construction of pFDi10

The erm-am gene of pVA891erm-am was inserted into pFDi9 to give pFDi10.

1 μg of pVA891erm-am was digested with XbaI+BamHI+ EcoRI (EcoRI was included to increase the frequency of the desired event). 1 μg of pFDi9 was digested with XbaI+ BamHI. The two digests were ligated and transformed into BR2027. Transformants were selected on LB agar supplemented with 10 μg/ml tetracycline (LB-tet). 50 colonies were streaked onto LB plates supplemented with 250 μg/ml erythromycin (LB-ery) and onto LB plates supplemented with 10 μg/ml chloramphenicol (LB-cam).

15 colonies were found to be resistant to all three antibiotics. Plasmid DNA was extracted from four of these triple-resistant transformants, and transformed into R594 and BR2026, respectively. The transformed cells were plated on LB-ery, LB-tet and LB-cam, respectively. All of these four plasmids gave tetR transformants of both strains. Chloramphenicol resistant transformants were for all four plasmids only obtained in strain BR2026 which showed that all four plasmids carried a cat-am gene unable to give chloramphenicol resistance in the non-suppressing strain R594.

Three of the four above plasmids gave erythromycin resistant transformants of BR2026, but none of R594, and one of the four plasmids gave erythromycin resistant transformants of both strains. The latter plasmid was discarded as having a reversion of the erm-am gene. One of the three plasmids having erm-am, cat-am and tet genes was kept as pFDi10.

EXAMPLE 2

Selection of nonsense suppressing strains of Lactococcus lactis using pFDi10

1. Transformation of pFDi10 into Lactococcus lactis MG1363

Competent cells of MG1363 were prepared and transformed by electroporation as described by Holo and Nes 1989. 10 μg of pFDi10 was precipitated by ethanol and the dried pellet resuspended in 10 μl of glass distilled sterile water. 40 μl competent cells of MG1363 was added and the mixture electroporated using a BioRad gene pulser using the settings of 25 μF, 2kv, 200Ω. The time constant obtained was 4.8. 960 μl ice-cold SGM17 broth was added and the mixture kept on ice for 5 minutes. The mixture was transferred to a tube containing 2 ml SGM17 broth and incubated at 30° C.

for 2 hours before dilutions made in SGM17 broth were plated on SGM17 agar plates supplemented with 10 μg/ml tetracycline. A transformation efficiency of $2 \times 10^5$ transformants/μg was obtained. One colony was purified by restreaking twice on GM17 agar plates supplemented with 10 μg/ml tetracycline. The resulting strain FD73 was verified to contain pFDi10 by extracting plasmid DNA as described by Israelsen and Hansen 1993. The plasmid extracted from FD73 had a size identical to pFDi10 and identical restriction pattern when digested with XbaI+BamHI. A sample of FD73 was deposited on 20 Sep. 1993 with DSM-Deutsche Sammlung von Mikroorganismen und Zellkulturen GmbH, Mascheroder Weg 1b, D-38124 Braunschweig Germany, under the accession number DSM 8557.

A culture of FD73 (MG1363/pFDi10) was prepared by inoculating a single colony of FD73 into 10 ml of GM17 supplemented with 10 μg/ml tetracycline followed by incubation at 30° C. for 18 hours. From this overnight culture 0.2 ml was plated on each of the following media: GM17+10 μg/ml tetracycline+5 μg/ml chloramphenicol+1 μg/ml erythromycin; GM17+5 μg/ml chloramphenicol; GM17+1 μg/ml erythromycin. From a $10^{-5}$ dilution of the overnight culture 0.1 ml was plated on GM17+10 μg/ml tetracycline. The plates were incubated at 30° C. for 42 hours. The results are summarized in Table 4.

TABLE 4

Cell counts in an overnight culture of FD73

| Medium | CFU/ml |
|---|---|
| tet | $1 \times 10^9$ |
| cam | $7 \times 10^1$ |
| ery | $7 \times 10^0$ |
| tet + cam + ery | 0 |

The results of this experiment show that neither the cat-am nor the erm-am gene of pFDi10 confer antibiotic resistance to MG1363, indicating that *Lactococcus lactis* MG1363 is not an inherently nonsense suppressing strain. The corresponding wildtype genes are expressed well in MG1363 as the plasmid pFDi6 give erythromycin and chloramphenicol resistance when transformed into MG1363.

2. The isolation of nonsense suppressing mutants of *Lactococcus lactis*.

*Lactococcus lactis* FD73 was mutagenized with EMS by the following procedure:
(i) 9 ml of GM17+10 μg/ml tetracycline was inoculated with a single colony of FD73 followed by incubation for 18 hours at 30° C.;
(ii) 270 μl of EMS was added to the above culture and the incubation continued for 100 minutes at 30° C.;
(iii) each of 10 tubes of 9 ml GM17 were inoculated with 0.9 ml of the EMS treated culture and subsequently incubated at 30° C. for 18 hours;
(iv) from each of the above tubes 0.2 ml was plated onto GM17 plates supplemented with 5 μg/ml chloramphenicol+1 μg/ml erythromycin. The plates were incubated at 30° C. for 42 hours;
(v) one colony from each of the above plates which contained 13 to 30 colonies was purified by streaking onto GM17 supplemented with 10 μg/ml tetracycline;
(vi) the resistance to chloramphenicol and erythromycin was verified by streaking on GM17 plates with erythromycin and chloramphenicol, respectively;
(vii) five colonies showing resistance to cam, erm and tet were selected for further analysis. All five were subsequently shown to be nonsense suppressing strains. In the following description data is only given for one of the five independent mutants. The mutant described in the following is designated FD87.

3. Identification of the localization of the suppressor gene in FD87

Plasmid DNA was extracted from an overnight culture of FD87 in GM17 supplemented with 10 μg/ml tetracycline. The plasmid extracted had, as expected, the same size as pFDi10. The restriction patterns obtained with BamHI and HindIII were also identical to the ones obtained with pFDi10. The plasmid extracted from FD87 was transformed into *E. coli* R594 (non suppressing) and tetracycline resistant transformants selected. The transformants were subsequently screened for resistance to erythromycin and chloramphenicol. All transformants screened were found to be sensitive to erythromycin and chloramphenicol. This result shows that the cat and erm genes of the plasmid still carry the amber mutation and thereby that the mutational event in FD87 was not a simultaneous reversion of both amber mutations on pFDi10.

FD87 was cured for the pFDi10 plasmid by inoculating 9 ml GM17 with 0.1 ml of a $10^{-6}$ dilution of a fresh overnight culture of FD87. This culture was incubated for 24 hours at 30° C. before plating 0.1 ml of a $10^{-6}$ dilution of this second culture on a GM17 plate. The plate was incubated at 30° C. for 18 hours. 169 colonies appeared on the plate and of these, 100 colonies were screened for resistance to tet, cam and ery by streaking onto GM17, GM17+tet, GM17+cam and GM17 +ery, respectively. 97 colonies had retained resistance to all three antibiotics and three colonies were sensitive to all three antibiotics.

One of the sensitive colonies was repurified by streaking on GM17 and this strain was designated FD100. Analysis for plasmid DNA of FD100 did not reveal any plasmids.

As the plasmid-cured variant FD100 is sensitive to cat and ery it could by concluded that the mutant FD87 did not acquire alternative antibiotic resistance genes. This strongly indicates that the mutation gave rise to a nonsense suppressor gene. This was proven to be the case by transforming FD100 with pFDi10 and selecting tetracycline resistant transformants as described above for MG1363. The transformants of FD100 was also found to be erythromycin and chloramphenicol resistant, showing that strain FD100 is a nonsense suppressor strain capable of suppressing both amber mutations of pFDi10 whereas the parent strain MG1363 is unable to suppress any of these two amber mutations of pFDi10.

A sample of FD100 was deposited on 20 Se. 1993 with DSM-Deutsche Sammlung von Mikroorganismen und Zellkulturen GmbH, Mascheroder Weg 1b, D-38124 Braunschweig Germany under the accession number DSM 8561.

EXAMPLE 3

Cloning of the suppressor gene from FD100

1. The construction of the cloning vector pFDi3 pFDi3 is an *E. coli-Lactococcus lactis* shuttle vector carrying a cat gene and an erm-am gene.

pFDi3 was constructed by cloning the erm-am gene of pVA891erm-am into pCI372. This cloning was done by digesting pVA891erm-am DNA with XbaI+BamHI+PvuII and digesting pCI372 with XbaI+BamHI as described in Example 1 for the construction of pFDi10.

When pFDi3 is transformed into Lactococcus lactic MG1363 only chloramphenicol resistant transformants are obtained as MG1363 is unable to suppress the erm-am mutation. This vector was used for the cloning of the nonsense suppressor gene of FD100 in MG1363 as it was expected that the cloning of the suppressor gene into pFDi3 would give a plasmid expressing erythromycin resistance in MG1363.

2. Cloning of the suppressor gene

Chromosomal DNA of FD100 was prepared from a fresh 100 ml overnight culture of the strain grown in GM17. The cells were harvested by centrifugation at 7000×g for 10 minutes. The cells were resuspended in TE buffer and harvested by centrifugation. The cell pellet was frozen and kept at −20° C. for 18 hours.

The pellet was thawed and resuspended in 3 ml STET buffer [8% w/v Sucrose, 5% v/v TritonX100, 50 mM EDTA (pH 8.0), 50 mM TrisCl (pH 8.0)]. 750 μl 10 mg/ml of lysozyme was added, and the mixture was incubated at 37° C. for 60 minutes. 750 μl 10% w/v SDS was added and incubation continued at 37° C. for 30 minutes followed by incubation at 65° C. for 30 minutes.

The solution was extracted with phenol:chloroform (1:1) three times. DNA was precipitated by adding NaCl to a final concentration of 0.5M and adding an equal volume of isopropanol. The precipitated DNA was wound around an inoculation loop, washed three times in 70% ethanol and resuspended in 500 μl TE-buffer. The DNA concentration was determined to be 1.8 μg/μl by measuring the absorbance at 260 nm.

3.5 μg chromosomal FD100 DNA was digested with HindIII. 12 μg pFDi3 DNA was digested with HindIII and treated with Calf Intestine Alkaline Phosphatase (Boehringer Mannheim) as described in Sambrook et al. 1989. The two mixtures were extracted with phenol and precipitated with ethanol and ligated as described in Sambrook et al. 1989. The ligated DNA was precipitated with ethanol and dissolved in 20 μl sterile distilled water and electroporated into *Lactococcus lactis* MG1363 as described by Holo and Nes 1989.

Transformants were selected on SGM17 supplemented with 1 μg/ml erythromycin and on SGM17 supplemented with 5 μg/ml chloramphenicol. The transformation efficiencies obtained were 20 erythromycin resistant transformants per μg DNA and more that $10^5$ chloramphenicol resistant transformants per μg DNA. A total of 241 erythromycin resistant transformants were obtained.

Plasmid DNA was prepared from 11 erythromycin resistant transformants. The plasmids were digested with HindIII and analyzed by electrophoresis on an 0.8% agarose gel. All of these 11 plasmids had acquired a 3.2 kb fragment. Two of the plasmids had also acquired other fragments.

Restriction analysis using HindII revealed the presence of a HindII site in the 3.2 kb HindIII fragment. The HindII digests also revealed that the nine clones carrying only a single new fragment all had the fragment in the same orientation relative to the vector. In order also to isolate clones with the opposite orientation we isolated plasmid DNA from an additional 20 transformants and found plasmids with the 3.2 kb HindIII fragment in the opposite orientation. pFDi11 is one of the plasmids with only a single new HindIII fragment of 3.2 kb and pFDi12 is a plasmid with the same 3.2 kb fragment inserted in the opposite orientation.

EXAMPLE 4A

The construction of a plasmid with an amber nonsense mutation in the replication region Four primers were synthesized for use in polymerase chain reaction synthesis of the desired DNA fragment. These had the following sequences:

Primer 1 (SEQ ID NO:2): 5' TGAATTCAGAG-GTTTGATGACTTTGACC 3'

Primer 4 (SEQ ID NO:3): 5' GGAATTCCTAACAAAA-GACTATTAACGC 3'

Amber 1 (SEQ ID NO:4): 5' AAACTCTAGAGCAAG-TATTCG 3'

Amber 2 (SEQ ID NO:5): 5' CTTGCTCTA-GAGTTTTTGTAG 3'

Primer 1 corresponds to nucleotides 610–621 and Primer 4 is complementary to nucleotides 2340–2361 of the citrate plasmid replication region (Jahns et al, 1991). Both primers contain EcoRI sites at their 5' end. Amber 1 and Amber 2 each contains two mismatches that introduce an amber codon in the coding sequence (SEQ ID NO:7) and create an XbaI site as shown in Table 5 below:

TABLE 5

Introduction of an amber mutation in repB of the citrate plasmid pAK49

```
                                        amber
amber 1              5'    AAA  CTC  TAG  AGC  AAG  TAT  TCG    3'
                           |||  |||  * *  |||  |||  |||  |||
     5'...   GAA  CTA  CAA  AAA  CTC  AAT  AGC  AAG  TAT  TCG  ATT ...3'

RepB...      glu  leu  gln  lys  leu  asn  ser  lys  tyr  ser  ile  ...

3'...   CTT  GAT  GTT  TTT  GAG  TTA  TCG  TTC  ATA  AGC  TAA ...5'
                       |||  |||  |||  |||  * *  |||  |||
amber 2              3'    GAT  GTT  TTT  GAG  ATC  TCG  TTC    5'
```

The primers, amber 1 (SEQ ID NO:4) and amber 2 (SEQ ID NO:5) are above and below the repB sequence (SEQ ID NO:7). The mismatched base pairs are indicated by *. The XbaI site introduced is underlined and the amber codon (TAG) introduced at codon 159 of repB indicated.

Polymerase chain reactions were done with Primer 1 and Amber 2 and with Primer 4 and Amber 1 using as the template pAK49, the citrate plasmid of *Lactococcus lactis* subsp. *lactis* biovar diacetylactis strain DB1138 cloned into pVA891 (Macrina et al, 1983). Fragments of 0.8 and 0.9 kb, respectively were obtained. These were digested with EcoRI and XbaI, mixed and cloned in EcoRI digested pIC19H (Marsh et al, 1984). Fifteen out of 18 clones analyzed had both fragments, joined at the XbaI site to give a 1.7 kb EcoRI fragment. The insert from one such clone was moved to pVA891 (Macrina et al, 1983) as a HindIII fragment producing pAK58 which contains an amber mutation in repB. This construction is illustrated in FIG. 2.

Electroporation of FD100 and MG1363 with pAK58 produced erythromycin resistant transformants with FD100 but not with MG1363 (however, see Example 4B). Accordingly, pAK58 only replicates in a nonsense suppressing strain confirming the presence of an amber mutation in repB.

EXAMPLE 4B

The isolation of a MG1363 strain suppressing the amber mutation in pAK58

Electroporation of pAK58 into MG1363 was done following standard procedures (Holo & Nes, 1989). As expected, pAK58 was unable to replicate in MG1363. Under conditions where a replicating citrate plasmid produced about 200,000 transformants, pAK58 yielded two. These two colonies were further analyzed and one was found to contain an intact pAK58 while the other contained no plasmid. The strain containing pAK58 was named NJ1/pAK58 and saved for further analysis.

A sample of NJ1/pAK58 was deposited on 20 September 1993 with DSM-Deutsche Sammlung von Mikroorganismen und Zellkulturen GmbH, Mascheroder Weg 1b, D-38124 Braunschweig Germany under the accession number DSM 8559.

Plasmid pAK58 was cured from NJ1/pAK58 by growing 30 generations without antibiotics. After plating and testing, 16% of the colonies tested were found to be free of pAK58. One of these was named NJ1 and further characterized. Electroporation of NJ1 with pAK58 yielded a high frequency of transformants, indicating that NJ1 contains a suppressor mutation allowing replication of pAK58 in spite of the amber mutation. This suppressor suppressed neither the nonsense mutations in pFDi10 nor the nonsense mutations in the phage φMPC100 derivatives (see Example 5). Thus this suppressor is different from the FD100 suppressor described hereinbefore.

EXAMPLE 4C

Cloning of the nonsense mutation suppressor gene from NJ1

Total genomic DNA was isolated from NJ1 following standard procedures (Johansen & Kibenich, 1992) and partially digested with Sau3A I. These fragments were ligated with BglII digested pAK58 and transformations of MG1363 were done. A DNA fragment of NJ1 containing the suppressor gene will allow replication of pAK58 in MG1363. One such clone was obtained and designated pAK85. The 5.1 kb of DNA of pAK85 was subcloned in pCI372 (Hayes et al, 1990) in a variety of ways and tested for suppression of the amber mutation in pAK58 by electroporation of MG1363 with a mixture of the pCI372 derivative to be tested and pAK58. One clone, pAK89.1, contains a 1.1 kb EcoRI-XbaI fragment and has suppressor activity. Sequencing of pAK89.1 has been done and revealed the suppressor gene to be a tRNA with an anticodon recognizing only amber codons. Thus, the suppressor is an amber suppressor. The DNA sequence coding for this tRNA is the following (SEQ ID NO:1):

1 GGAGCCATGG CAGAGTGGTA ATGCAACGGA CTCTAAATCC GTCGAACCGT
51 GTAAAGCGGC GCAGGGGTTC AAATCCCCTT GACTCCTTA

The final three base pairs are expected to be replaced with CCA post-transcriptionally.

Homology searches of the EMBL DNA sequence data bank, release 34.0 revealed that this tRNA most likely is a serine tRNA. The DNA sequence of the wild-type tRNA gene in MG1363 was determined by PCR amplifying a 450 bp sequence containing this gene, followed by sequencing of the amplified fragment. The tRNA gene mutated in NJ1 was confirmed to be a serine tRNA gene with the anticodon 5' CGA 31 in the wild type and 5' CTA 3' in the mutant.

A sample of MG1363/pAK85 was deposited on 20 Sep. 1993 with DSM-Deutsche Sammlung von Mikroorganismen und Zellkulturen GmbH, Mascheroder Weg 1b, D-38124 Braunschweig Germany, under the accession number DSM 8558.

EXAMPLE 5

The isolation of nonsense mutants of the prolate headed lactococcal phage φMPC100

φMPC100 is a prolate Lactococcus phage from the phage collection of Chr. Hansen's Laboratorium A/S. This phage gives large plaques (diameter 2–4 mm) when plated on MG1363. This phage was used for the isolation of mutants with nonsense mutations in genes essential for phage development. Such mutants will be unable to form plaques on MG1363, but capable of growing on FD100.

A phage stock of φMPC100 with a titre of $1.8 \times 10^{10}$ plaque forming units (PFU)/ml was used for the preparation of a mutagenized phage stock. The mutagenesis was done using hydroxylamine treatment of the phage stock as described in Silhavy et al. 1984. The hydroxylamine treatment of φMPC100 for 22 hours reduced the titre with the same order of magnitude as described for $E.$ $coli$ phages. The survival rate for φMPC100 was $3 \times 10^{-3}$.

Dilutions of the mutated phage stock was plated for plaques on strain FD100 by mixing 10 μl of phage dilution, 200 μl of a fresh overnight culture of FD100 in GM17 supplemented with 10 mM $CaCl_2$ and 10 mM $MgSO^4$ and 3 mlM17 of soft agar supplemented with 10 mM $CaCl_2$ and 10 mM $MgSO_4$. (The soft agar had been melted by boiling and cooled to 42° C.)

The mixture was poured onto a GM17 agar plate and incubated at 30° C. for 18 hours. On the plate with mutagenized phages plaques of normal size as well as small plaques were observed. 81 plaques were isolated by removing agar plugs containing a plaque with a sterile Pasteur pipette. The agar plugs were transferred to 200 μl M17+10 mM $CaCl_2$+10 mM $MgSO_4$ and phages allowed to diffuse out of the agar for 2 hours at 8° C.

15 μl of each of the 81 phage stocks were spotted onto two plates with lawns of FD100 and MG1363, respectively. Three of the 81 phages were found to grow only on FD100 whereas the remainder grew equally well on both strains.

The three mutant phages which were designated φMPC100a12, φMPC100a16 and φMPC199a77 were purified by plating to single plaques twice on strain FD100. On FD100 the mutant φMPC100a77 gives small plaques and the two others give plaques of normal size. A sample of φMPC100a77 was deposited on 20 Sep. 1993 with DSM-Deutsche Sammlung von Mikroorganismen und Zellkulturen GmbH, Mascheroder Weg 1b, D-38124 Braunschweig Germany under the accession number DSM 8562.

The reversion frequencies of the three phage mutants were determined by titration of phage stocks on the permissive host FD100 and on the nonpermissive host MG1363.

TABLE 6

Reversion frequencies of φMPC100 nonsense mutants

| | Titre (PFU/ml) on: | | Reversion frequency |
|---|---|---|---|
| | FD100 | MG1363 | |
| φMPC100a12 | $1.5 \times 10^6$ | $0.6 \times 10^2$ | $4 \times 10^{-5}$ |
| φMPC100a16 | $4.8 \times 10^6$ | $9.10^2$ | $2 \times 10^{-4}$ |
| φMPC100a77 | $8.7 \times 10^6$ | $7 \times 10^2$ | $8 \times 10^{-5}$ |

To verify that the phage mutations are suppressed in FD100 by the same suppressor as the erm-am mutation used for the selection of FD100 it was examined if the phage mutants were able to grow on MG1363 with pFDi11 or pFDi12.

It was found that introduction of either pFDi11 or pFDi12 makes MG1363 a permissive host for the phage mutants above. It can thus be concluded that the suppressor cloned in pFDi11 and pFDi12 is capable of suppressing the erm-am mutation as well as the phage mutations. This proves that the phage mutants are nonsense mutants.

EXAMPLE 6

Determination of the size of the suppressor gene of FD100

Since a suppressor tRNA gene is smaller than 100 bp it was aimed at determining the location of the suppressor gene on the 3.2 kb fragment inserted in pFDi11 and pFDi12.

From pFDi11 a total of 3.7 kb was deleted thereby removing the erm-am gene and 2.2 kb of the inserted fragment. The resulting plasmid pFDi13 retains 1.0 kb of the original insert. From pFDi12 a total of 2.5 kb was deleted thereby removing the erm-am gene and 1.0 kb of the inserted fragment. The resulting plasmid pFDi14 retains 2.2 kb of the original insert.

pFDi13 and pFDi14 were constructed by digesting pFDi11 and pFDi12 respectively with HindII. The digested DNAs were extracted with phenol, precipitated and ligated (separately). The ligation mixtures were transformed into R594 as described in Sambrook et al. 1989. Selection of transformants were made on LB supplemented with 10 μg/ml chloramphenicol.

Three transformants from each experiment were analyzed. All three transformants from the pFDi11 experiment were identical and one was kept as pFDi13. All three from the pFDi12 experiment were identical and one was kept ad pFDi14. pFDi13 and pFDi14 were transformed into MG1363 by electroporation selecting for chloramphenicol resistant transformants.

The presence or absence of the suppressor gene on pFDi13 and pFDi14 was determined by testing for suppression of the phage mutant φMPC100a12. The results are given in Table 7.

TABLE 7

Suppression of nonsense mutations of φMPC100a12

| Strain | Growth of φMPC100a12 |
|---|---|
| MG1363 | − |
| FD100 | + |
| MG1363 pFDi11 | + |
| MG1363 pFDi12 | + |
| MG1363 pFDi13 | − |
| MG1363 pFDi14 | + |

These results show that the suppressor is carried on the 2.2 kb fragment of pFDi14.

In order to determine the location of the suppressor gene even more precisely deletions were made in the plasmid pFDi14 using the Erase-a-Base system from Promega. The Erase-a-Base system generates unidirectional deletions in a plasmid by using ExonucleaseIII. The deletions are forced to be unidirectional by linearizing the plasmid with two restriction enzymes of which one is generating 3' overhangs (ExonucleaseIII resistant). 5 μg pFDi14 DNA was digested with SacI (ExonucleaseIII resistant 3' overhangs) and BamHI (ExonucleaseIII sensitive 5' overhangs). The treatment with ExonucleaseIII at 30° C., sampling with intervals of 1 minute from 1 to 15 minutes after addition of ExonucleaseIII, treatment with S1 nuclease, treatment with Klenow fragment of DNA polymerase and ligation were done exactly as described in the Erase-a-Base manual from Promega.

Each of the ligated samples were transformed into *Lactococcus lactis* MG1363 by electroporation. Transformants were selected on SGM17 agar supplemented with 10 μg/ml of chloramphenicol. Transformants were obtained from every sample. 20 colonies from each of the five last samples (expected to carry the largest deletions) were tested for suppression of φMPC100a12.

Of the 100 colonies tested only five retained the suppressor (2 from the 12 minutes sample, 2 from the 14 minutes sample and 1 from the 15 minutes sample).

Plasmid DNA was extracted from several suppressing and nonsuppressing transformants. The two smallest plasmids still having the suppressor were named pFDi17 and pFDi18. The largest plasmid (although smaller than pFDi17 and pFDi18) not carrying a suppressor was pFDi19.

The length of the chromosomal insert was found to be 266 bp for pFDi17 and pFDi18. The fragment retained in pFDi19 was 11 bp shorter (see Example 7).

EXAMPLE 7

Nucleotide sequence of the nonsense suppressor gene of FD100

The DNA sequence of the insert derived from FD100 in each of the three plasmids pFDi17, pFDi18 and pFDi19 was determined using the sequenase kit from USB, Cleveland, Ohio, USA. The protocol supplied with the kit for sequencing double stranded plasmids was followed. For each plasmid the sequence of both strands was determined. The sequence of one strand was determined using the primer 5' GCTAGAGTAAGTAGTT 3' (primer # 1206 from New England Biolabs, Beverly, Mass., USA) (SEQ ID NO:8), the sequence of the other strand was determined using the primer 5' CCTTTACCTTGTCTACAAACC 3' (SEQ ID NO:9).

pFDi17 and pFDi18 contained fragments with the same length and sequence. pFDi19, which did not express suppressor activity contained a fragment which was found to be 11 bp shorter than the fragment in pFDi17 and pFDi18 (cf. FIG. 3).

The sequence of the fragment carrying the suppressor gene was compared to all nucleotide sequences present in the EMBL-database release 34 using the Fasta program of the GCG program package (Devereux et al. 1984, Nucleic Acids Research, 12, 387–395). The sequence showing the highest homology to the sequence of FIG. 3 was the sequence of tRNA-gln of *Bacillus subtilis*. 19 other tRNA-gln genes from bacteria, chloroplasts and mitochondria also showed extremely high homologies.

Figure 5A:
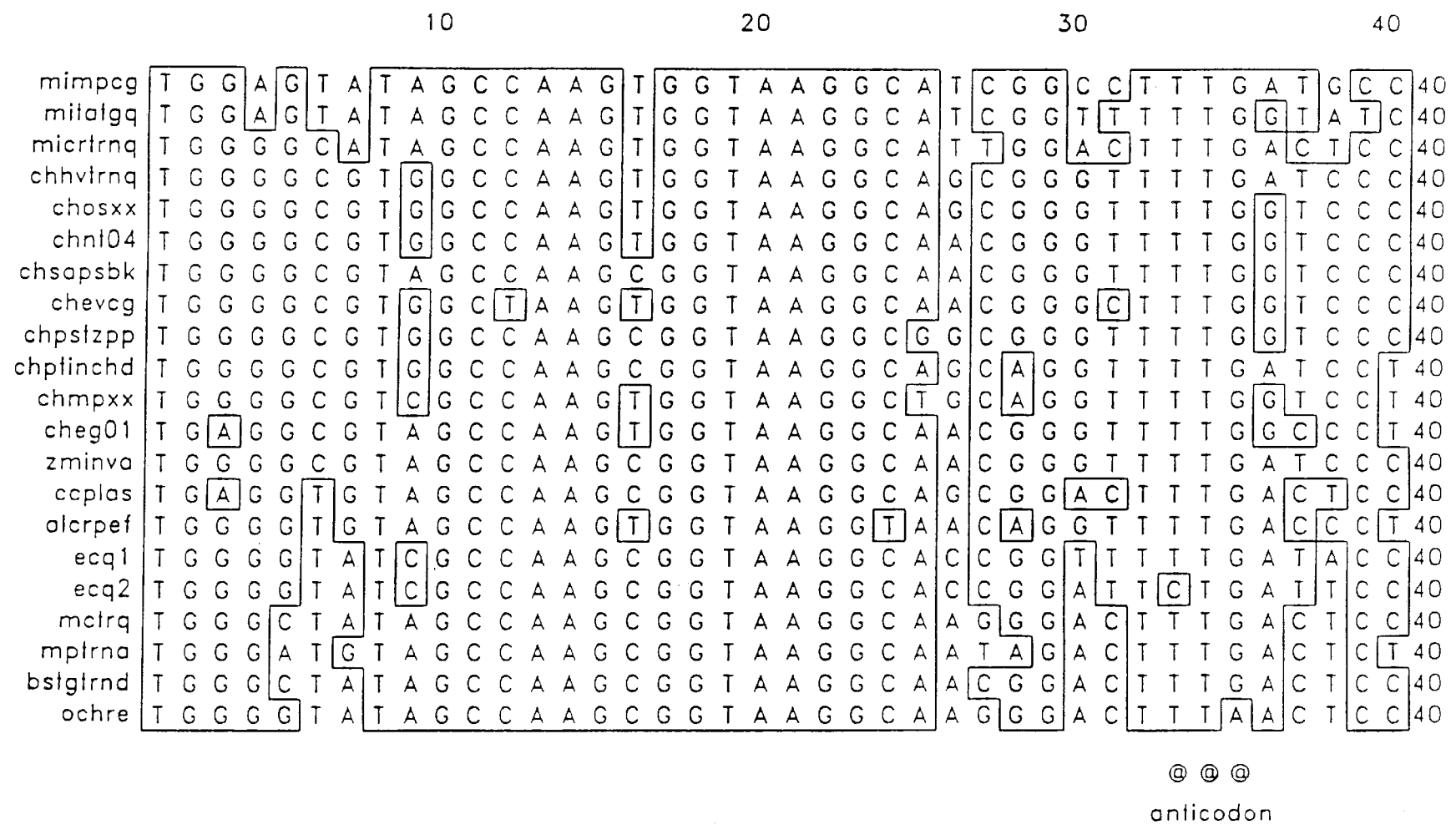
Figure 5B:
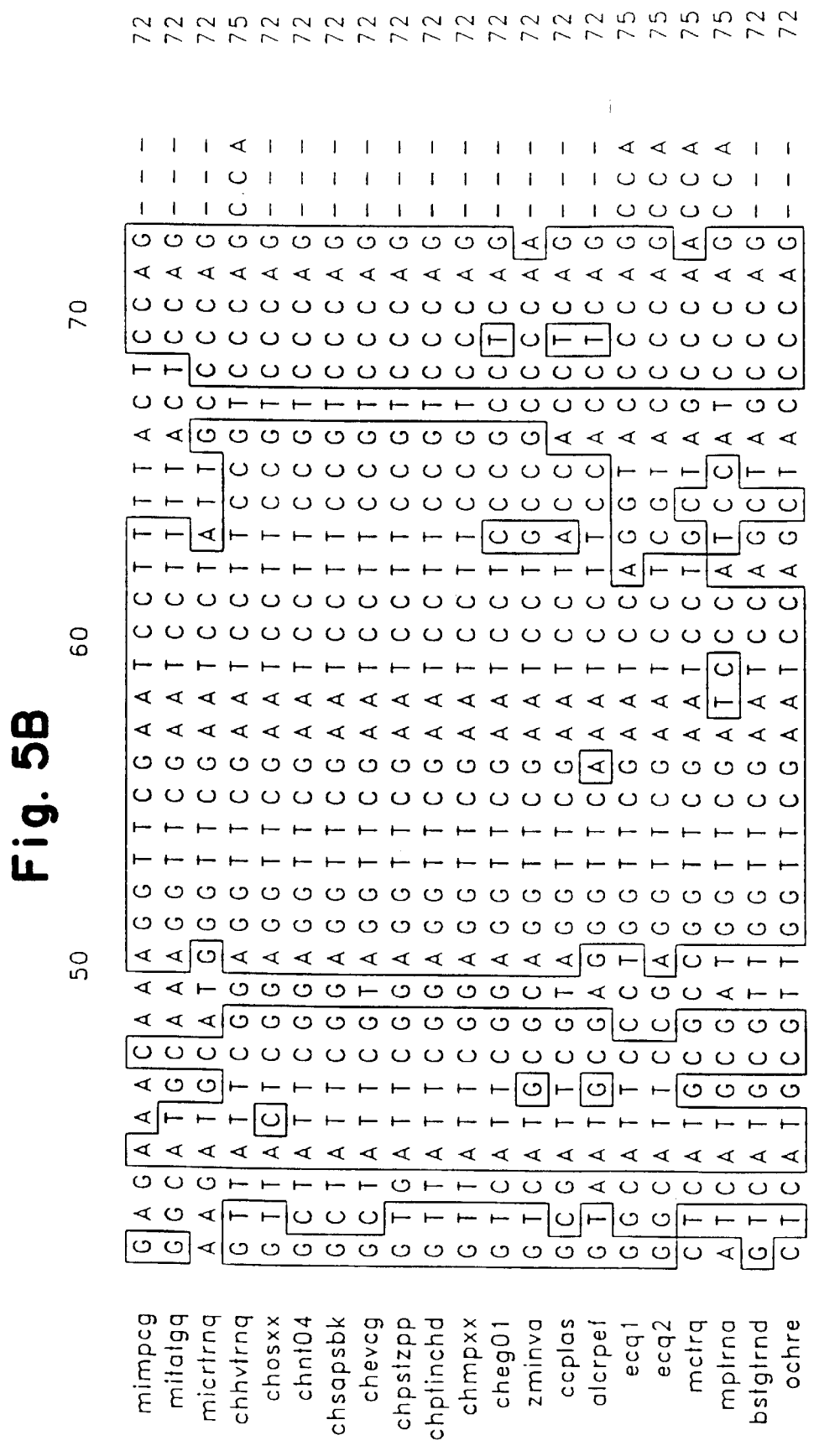

The alignment of the FD100 suppressor gene with 20 -tRNA-gln genes is presented in FIG. 5. This shows that the suppressor gene is a tRNA-gln gene. At the position of the anticodon the FDi100 suppressor tRNA-gln has the triplet 3' ATT 5' instead of the usual gln anticodons 3' GTT 5' or 3' GTC 5'. This shows that the suppressor tRNA-gln is an ochre suppressor recognizing the stop codon 5' UAA 3' as a gln codon. However, this ochre suppressor does also recognize the amber stop codon 5' UAG 3' (cf. Example 5) probably due to wobble basepairing at the third position of the codon.

Sequencing of the wild type gene has subsequently revealed that this gene is a tRNA-gln gene with the anticodon 3' GTT 5'. Sequencing of this tRNA-gln allele from the suppressor mutants described in Example 2 revealed that not all suppressor mutants were of this type. It is therefore expected that further analyses of the other mutants will reveal suppressors with other specificity.

The 11 extra basepairs in pFDi17 and pFDi18 compared to pFDi19 contain a sequence resembling the −35 part of a consensus promoter. The suppressor gene of pFDi19 is not expressed, probably due to the lack of a promoter. The plasmid pFDi19 may assumingly be used to construct suppressor genes with regulated or altered expression.

EXAMPLE 8

Isolation of purine auxotrophic mutants and suppression of two mutations in *Lactococcus lactis* located in pur genes, by a nonsense suppressor gene.

*Lactococcus lactis* purine auxotrophic mutants were isolated. Introduction of a nonsense suppressor gene into *Lactococcus lactis* pur mutants resulted in prototrophy.

In general, the de novo synthesis of purine nucleotides from small precursors requires 10 enzymatic reactions leading to inosine monophosphate (IMP). IMP is used in the synthesis of both AMP and GMP. Purine bases, originating intracellularly or from exogenous sources, and nucleosides are converted to nucleotides via salvage pathways which have been shown to be distinct among different organisms (for reviews see: Nygaard 1983; Neuhard and Nygaard 1987). Virtually nothing is known about the purine metabolism in the anaerobic gram-positive bacterium *Lactococcus lactis* (Nilsson and Lauridsen, 1992). In the following is described the isolation of purine auxotrophic mutants and how they can be used in combination with suppressor genes.

1. Materials and methods

1a. Bacterial strains and media used.

The plasmid-free Lactococcus lactis strain MG1363 (Gasson, 1983) was grown in M17 medium (Oxoid) or in a defined medium having the same composition as the phosphate-buffered minimal medium of Clark and Maaløe (1967) except that the NaCl of this medium was replaced by the same weight of sodium acetate (DN-medium). As carbon source in M17 medium or DN medium 0.5% glucose was used. For selection purposes, chloramphenicol 5 mg/L of medium was used. Purine compounds as supplements were added, when appropriate in the following concentrations: adenine, hypoxanthine, guanine and xanthine, 15 mg/mL; adenosine, inosine and guanosine 30 mg/L.

1b. Isolation of purine auxotrophic *Lactococcus lactis* strains.

MG1363 was grown overnight in M17 medium. 1/33 vol ethyl methane sulphonate (EMS, Merck) was added and the culture incubated further 2½ hours at 30° C. The culture was divided and diluted 50 fold in fresh DN-medium containing hypoxanthine to give five cultures which were subsequently grown overnight. DN-medium containing hypoxanthine was inoculated with mutagenized culture to $2 \times 10^7$ bacteria/ml and grown to $8 \times 10^7$ bacteria/ml. The cells were harvested, washed twice in DN medium without hypoxanthine and resuspended to $4 \times 10^6$ bacteria/ml in DN medium and incubated for 2 hours at 30° C. Ampicillin was added to a final concentration of 100 µg/ml and the culture was further incubated for 5 hours. The cells were harvested by filtration (Millipore, size 0.2 µm), washed 3 times with DN medium, and suspended in 1/10 vol DN medium containing hypoxanthine. 50 µl culture ($2 \times 10^4$ viable bacteria/ml) was spread onto DN hypoxanthine-containing agar plates and incubated overnight. 582 colonies from each culture were screened for growth with and without hypoxanthine on DN-medium agar plates.

1c. DNA manipulation.

*Lactococcus lactis* plasmid DNA was isolated according to the method of Johansen and Kibenich (1992). *Lactococcus lactis* was transformed by electroporation as recommended by Holo and Nes (1989). The Lactococcus lactis plasmids pFDi17 and pFDi19 as described above were used.

2. Isolation of purine auxotroph mutants

Five mutants (DN207–211) of strain MG1363 with a purine auxotrophic phenotype was isolated as described above in materials and methods. Exogenously supplied adenine, hypoxanthine, xanthine, guanine or the ribonucleosides adenosine, inosine and guanosine, restored growth of DN207–211.

3. Suppression of pur mutations in DN207–211 by the nonsense suppressor gene.

The two plasmids pFDi17 (sup$^+$) in which an ochre suppressor is expressed, and pFDi19 (sup$^-$) not expressing a suppressor, were transformed into the DN207–DN211 strains followed by selecting for chloramphenicol resistance on M17 agar plates. Transformants were screened for growth with and without hypoxanthine on DN medium agar plates. The plasmid pFDi17 (sup+) could transform DN209 and DN210 to Pur$^+$, whereas pFDi19 (sup-) could not. In all the other strains none of the plasmids could transform the cells to Pur$^+$. This shows that the mutations causing the purine auxotrophic phenotypes in DN209 and DN210 were nonsense mutations.

These experiments have shown that it is possible to isolate auxotrophic mutants in *Lactococcus lactis* (here purine auxotrophic mutants are used as a model system) and to screen these for nonsense mutations that can be restored by introducing suppressor genes into the cells. The significance of these findings is that such a system may be used for maintenance of plasmids (like pFDi17) e.g. during fermentation in media that do not support growth of the auxotrophic mutants unless the auxotrophy is restored by a plasmid containing a suppressor gene. The advantage may be to use one and the same suppressor gene for suppression of amber/ochre nonsense mutations located in a variety of distinct genes of *Lactococcus lactis* strains.

The one and same suppressor gene may also be used to control expression of various gene products, as in the example with the pur gene products in the strains DN209 and DN210. In these strains, the pur gene products are only expressed if the suppressor gene is introduced into the cells.

A sample of DN209/pFDi17 was deposited on 20 Sep. 1993 with DSM-Deutsche Sammlung von Mikroorganismen und Zellkulturen GmbH, Mascheroder Weg 1b, D-38124 Braunschweig Germany under the accession number DSM 8560.

4. Stability of pFDi17 in *Lactococcus lactis* strain DN209

Cultures of *Lactococcus lactis* strain DN209 containing pFDi17 (sup+) or pFDi19 (sup−) were grown for about 100 generations in 9.5% LAB-milk (9.5% skim milk powder in water) containing 0.5% purine-free casamino acids as the basal medium. A culture of DN209/pFDi19 and one culture of DN209/pFDi17 was grown in the basal medium supplemented with 15 mg/l of hypoxanthine as a purine source, and one culture of DN209/pFDi17 was grown in the basal medium only.

DN209/pFDi19 cannot grow in milk not containing a purine source, but by adding a purine source it may be possible to observe losses of the plasmid during growth. DN209/pFDi17 was capable of growing in the basal medium supplemented with the purine source as well as in the basal medium without such supplementation. Under these experimental conditions, no losses of plasmids were observed in any of the DN209/pFDi17 cultures or in the DN209/pFDi19 culture.

EXAMPLE 9

Strategy for the provision of nonsense suppressing Leuconostoc spp

It is suggested that Leuconostoc spp comprising a nonsense suppressor-encoding gene may be provided by carrying out the following experiments:

In a first step it is determined which of commonly used replicons can be used to transform Leuconostoc spp. including *Leuconostoc lactis* and *Leuconostoc cremoris* e.g. by electroporation of competent cells. Replicons to be tested include the citrate plasmid replicon (pKR46), the pCI305 replicon (pCI3340) and the pSH71 replicon (pNZ18). If the citrate plasmid replicon works, pAK58 may be used to isolate suppressors; if the pCI305 replicon works, pFDi10 can be used to select suppressors. If none of the suggested replicons work, a new selection plasmid must be constructed e.g. as outlined in the following.

The chloramphenicol resistance gene from pNZ18 is eliminated and replaced with the tetracycline resistance gene and the ery-am and cam-am markers from pFDi10. It is contemplated that the easiest way to achieve this would be to clone the 3.2 kb BglII fragment from pNZ18, containing the replication origin, into the BglII or BamHI site of pFDi10. This requires that the pCI305 and pSH71 origins can coexist on the same plasmid. If this is not the case, the pCI305 replicon may be inactivated by digesting with PacI, flushing the ends with DNA polymerase and ligating. This will introduce a −2 frameshift into the repB gene.

In a subsequent step an amber suppressor Leuconostoc spp may be selected by introducing the new plasmid into e.g. *Leuconostoc lactis* DB1164 or *Leuconostoc cremoris* DB1165 and selecting for tetracycline resistance followed by selecting mutants which are simultaneously resistant to erythromycin and chloramphenicol (following mutagenesis, if necessary), curing any interesting plasmid and confirming the antibiotic resistance is lost and reintroducing the selection plasmid and confirming that antibiotic resistance is regained. This will only occur if suppression is occurring.

EXAMPLE 10

The construction of DFG1, a food grade cloning vector

1. Introduction

In order to use genetically manipulated microorganisms in food products, vectors that are derived totally from the organism to be manipulated are desirable. A useful vector contains a replication region, a selectable marker and a multiple cloning site allowing insertion of desirable genes. In addition, it should be small enough to allow insertion of desired DNA without difficulty.

A food-grade cloning vector, pFG1 replicating in lactic acid bacteria was constructed which is based totally on DNA sequences from Lactococcus, and synthetic sequences. pFG1 contains the replication region of the *Lactococcus lactis* subsp. *lactis* biovar diacetylactis citrate plasmid, the ochre suppressor tRNA gene from *L. lactis* strain FD100 allowing selection of transformants of *Lactococcus lactis* DN209 (Example 8), and a synthetic polylinker with 11 unique restriction sites, identical to that found in vector pIC19R (Marsh et al., 1984).

The usefulness of pFG1 was demonstrated by cloning the pepN gene from *Lactococcus lactis* ssp. *cremoris* Wg2 (Strømann, 1992) to obtain the plasmid pFG2. A strain containing pFG2 contains 4–5-fold as much lysine aminopeptidase activity as the same strain containing only pFG1, and pFG2 is the first member in a new line of genetically manipulated lactic acid bacterial flavor control cultures.

2. Bacterial strains, plasmids and media

MG1363 is a plasmid-free derivative of *Lactococcus lactis* strain NCDO 712 (Gasson, 1983). FD100 is a mutant of MG1363 containing an ochre suppressor. DN209 is a purine auxotroph of MG1363, suppressible by the ochre suppressor. Wg2 is a wild-type strain of Lactococcus lactis ssp. *cremoris*. *Escherichia coli* DH5α was used for some cloning steps.

The cloning vector pIC19H [ampicillin resistance; Amp$^R$] (Marsh et al., 1984) was used throughout. The construction of the food-grade vector and cloning of the pepN gene are described below.

Lactococcus strains were grown at 30° C. in minimal medium (Recipe 053 of Genetics Department, Chr. Hansen's Laboratorium) containing 1% M17. *E. coli* strains were grown in LB medium at 37° C. Ampicillin was used at 50 μg/ml. Lysineaminopeptidase activity was assayed using the standard procedure of Chr. Hansen's Laboratory (Analytical Procedure P019).

3. Plasmid preparations and transformations

Plasmid DNA for sequencing and electroporations was prepared with the Qiagen plasmid kit (Diagen, Dusseldorf, Germany). Small scale plasmid preparations from Lactococcus were done according to Recipe 039 of Genetics Department, Chr. Hansen's Laboratorium. Plasmids were introduced into Lactococcus by electroporation of glycine-grown competent cells (Holo and Nes, 1989, Recipe 018 of Genetics Department, Chr. Hansen's Laboratorium).

4. Construction of the food-grade cloning vector pFG1

4.1. Cloning of the citrate plasmid replication region

Polymerase chain reaction (PCR) was done with two primers designed to amplify the entire replication region of the citrate plasmid as a 1.7 kb fragment. The primers had EcoRI sites at the 5' end and the resulting fragment was cloned into pIC19H to give pKR41 (FIG. 6). This clone has been described previously (Pedersen et al., 1994).

The replicon comprises the origin of replication and the repB gene of the citrate plasmid of L. lactis subsp. lactis biovar diacetylactis. Flanking sequences totalling 300 bp from the same plasmid are also included as are two synthetic linkers which contribute a total of 6 bp to this fragment.

4.2. Cloning of the ochre suppressor gene

The selectable marker is the supB gene of L. lactis strain FD100. This DNA fragment is 208 bp and has a sequence identical to that found in FD100 except for the presence of two linkers contributing a total of 6 bp.

The ochre suppressor gene of strain FD100 has been cloned and is contained on a plasmid called pFDi18 (Example 6). PCR using two primers (Ochre-1, CGAAT-TCATAAATGCTTTCCCCTATTC (SEQ ID NO:33); and Ochre-2, CGAATTCTTGAAATTTATGAGGGTTTTTGG (SEQ ID NO:34)) on pFDi18 resulted in a 208 bp EcoRI fragment containing the ochre suppressor gene. This fragment was cloned into pIC19H to give pAK95 (FIG. 6).

4.3. Combining the replication region with the suppressor gene

Plasmids pKR41 and pAK95 were digested with EcoRI, mixed, ligated and used to electroporate DN209, selecting on minimal medium. Transformants with plasmids containing at least the citrate plasmid replication region and the suppressor gene will form colonies. Some recombinant plasmids will also contain pIC19H. Colonies were scraped off the selection plates and plasmids extracted. Plasmids in this pool containing pIC19H were obtained by transforming DH5α, selecting amp$^R$ colonies.

Analysis of plasmids from seven amp$^R$ transformants revealed that all had pIC19H, the 1.7 kb EcoRI fragment from pKR41 and the 208 bp EcoRI fragment from pAK95. This was expected because the double selection used will give only plasmids containing all three fragments. One clone was saved as pAK102 (FIG. 6).

4.4. Deletion of the nonfood-grade components of pAK102

The final step in the construction of the food-grade cloning vector was the elimination from pAK102, of all of pIC19H except for the multiple cloning site. This was done by digesting with HindIII, self ligating and electroporating DN209 on minimal medium. All 20 colonies analyzed had the desired plamsid. One strain was saved and deposited in the culture collection as CHCC3061. The plasmid contained in this strain was named pFG1 and is the food-grade vector. pFG1 has a total size of 2003 bp The multiple cloning site (polylinker) is identical to that in a vector called pIC19R (Marsh et al., 1984) and is shown below (SEQ ID NO:35). The polylinker is 69 bp and was synthesized totally in vitro by Marsh et al. (1984). All sites are unique except for EcoRI and ClaI.

```
                                        H
                                        i
    E           B                       n                    B           E           E
    c     S     a     S           p     d        N     XS    g     X     c     C     c
    o     m     m     a           a     I        r     ha    l     b     o     l     o
    R     a     H     l           t     I        u     oc    I     a     R     a     R
    I     I     I     I           I     I        I     II    I     I     V     I     I
    GAATTCCCGGGGATCCGTCGACCTGCAGCCAAGCTTTCGCGAGCTCGAGATCTAGATATCGATGAATTC
1   ---------+---------+---------+---------+---------+---------+---------   69
    CTTAAGGGCCCCTAGGCAGCTGGACGTCGGTTCGAAAGCGCTCGAGCTCTAGATCTATAGCTACTTAAG
```

The selectable marker can, so far, only be used in DN209 which is a derivative of MG1363. MG1363 is a plasmid-free derivative of NCDO 712 and is therefor Lac$^-$ and Prt$^-$. In order to use pFG1 in other lactic acid bacterial strains, mutations suppressible by the ochre suppressor will be needed. Preferred mutations will be in genes in purine or pyrimidine biosynthesis because milk does not contain sufficient amounts of these compounds to support the growth of such mutants, thus making milk a selective medium for the mutants. Such mutants can be isolated by mutagenesis and enrichment techniques currently in use in the Department of Genetics of Chr. Hansens' Laboratorium. Plasmids constructed using DN209 can then be easily transferred into these mutants, resulting in new genetically manipulated lactic acid bacterial strains, including Lactococcus strains useful for a variety of cultures.

The DNA sequence of pFG1 (SEQ ID NO:36) is shown below:

| | | | | | |
|---|---|---|---|---|---|
| 1 | GAATTCCCGG | GGATCCGTCG | ACCTGCAGCC | AAGCTTTCGC | GAGCTCGAGA |
| 51 | TCTAGATATC | GATGAATTCC | TAACAAAAGA | CTATTAACGC | TTAATTCTTC |
| 101 | ATTTTTTCTT | GTCGATTTTC | GGTCGGTTGA | ACTTTTTTA | TTTTTGTTAG |
| 151 | TCTTTTTTTG | ATAAACTTTT | GTTCTTCAAG | GTTTAGGACG | ATCGAACCAC |
| 201 | TATTGTTTTT | TTGTCGATTT | TCGGTCGGCA | AAAACTTTAA | ATGGTATTGA |
| 251 | ACGGTCTGTT | TAGCTAGTCC | TAGCTCGTCC | GCCAACTCTT | TTATCGTTTT |

-continued

| | | | | |
|---|---|---|---|---|
| 301 TAAGTCTTCA | CTCATGGTTT | AAGTCCTGCC | TTTTAACCGT | TGGCAGATAT |
| 351 TGTTCAATGG | CTTTTTTAAG | ATATTTCGCT | ACATTACGTT | TAGAATAGGC |
| 401 TTCTTTTTTG | CTGGCAACAT | AAGACAAGTG | GTCTTTGACA | CCATTTAGCC |
| 451 CTCTTAATTC | TTTCAGTTCG | TCATAAAGCG | GATAAACATT | CTTCTGTAAG |
| 501 CCTACCATTG | TGGCTGTATC | CATAATATCA | TTCATGCCAA | TTAAGAAATT |
| 551 TTCAGATAAA | AGTCTTGTAT | ATTTACTTTC | CATTGCCTGT | TTTAGTAAGT |
| 601 CAGCTTCATT | TCTTGATTTT | TGCTTTTTAT | CGTCTTGATA | GTCTTTATCT |
| 651 CCCAACTTGT | AACTGTTATC | GTCTGCCATG | CGTTTCTTCT | CAATATGAAA |
| 701 GACAATAGAG | TCAATGCTCC | GCCCTGCTTT | CTTTTTCTCA | TAGGTTACAT |
| 751 TAAAAGAGGT | GTGAGCGTTG | ATTTCTTCAA | TTGCTTTTTT | TAATACTCTA |
| 801 GTTTCAAAAT | GGGGAAAATG | TTGATGTTCA | TTTATTGTAT | CAGTTATTTC |
| 851 TCGCAATTCT | TTCACTTTTA | TTGAGGGGTT | GCGGTAGGAT | TCCACTTGTT |
| 901 CAACTCTCCG | TCCCCCTTTC | ACGCTGTAAT | GTTCGTATTG | GTTATAATTC |
| 951 ATGGATAACC | AACGATACAA | AATAATCGAA | TACTTGCTAT | TGAGTTTTTG |
| 1001 TAGTTCGGAA | ATTTTATATT | GAGTAAATTC | TGCCTTTAAA | TCAATCAGAT |
| 1051 AGGGCATAAT | GGCTTGGTCA | AAACGTATTG | TTACTTCATC | GTTATAATCG |
| 1101 TTCCATTTTA | CATAAGGAAT | AGGCACAATG | CTTTCATACT | CAATACCTAG |
| 1151 TTTCTTATCA | GCTTTAATAT | TGAAAAAGGC | TTGCTTTTGC | ATATAATTAA |
| 1201 CTGCTTCTTT | GAATTGACTA | TGCTTACTGC | TAGACGATAC | TTCAAAAAAT |
| 1251 TTAAAAAGTT | CAGATTTTAA | AAGATAAACA | GTATTATTTT | TTGGGGGTTC |
| 1301 TTCGGTATCA | ATACAAGACA | CGGCTAACTC | AAACATTTTT | AAAGCTGTTT |
| 1351 TTTGCATTTT | AGCCACACTT | TGAATTAAAG | CGTTATGCTC | CACTACTTTG |
| 1401 CGTTTTTCTA | ATTCATTCAA | GGTCAGCACC | TGCTTTTGTT | TGTTTTGTTT |
| 1451 TTCTTGGTATA | ATCATAGTAT | AAATACGCTC | CTTTGCGTGT | TTTAGTAGTA |
| 1501 GCATAGAGAA | AGTCATTTCA | TAGTGAGTTT | TCTCTATGCT | TTTATTATAC |
| 1551 TATATACAGT | ACACAAATAC | AAAAGTCGTG | CTGTGTACAT | CGATTTTTGT |
| 1601 GACTCTATAC | ATCGATTTTT | GTGACTCTAT | ACATCGATTT | TTGTGACTGT |
| 1651 TTAATTTCTA | TAACTAGCGA | AAACACTGCC | TTTTTTTTCA | CGCAAAAGAA |
| 1701 CAAAAGATTA | AAATATATAT | GATAAATATA | TAGTAGGCTT | CGCCTTTTTT |
| 1751 TATTTTTTTC | AAAAATTTAA | AACCAAAGGT | CAAAGTCATC | AAACCTCTGA |
| 1801 ATTCTTGAAA | TTTATGAGGG | TTTTTGGTAA | AATATTTCTT | GTCGTCATCA |
| 1851 AGCGATCTTG | GGGTATAGCC | AAGCGGTAAG | GCAAGGGACT | TTAACTCCCT |
| 1901 CATGCGTTGG | TTCGAATCCA | GCTACCCCAG | TAAAAAAACT | TTAAAGGAAA |
| 1951 CGTTGTTTCC | TTTTTTCTTT | TTACTAAAAT | ATGATAGAAT | AGGGGAAAGC |
| 2001 ATTTAT | | | | |

A strain of DN209/pFG1 was deposited on 6 May 1994 under accession No. DSM 9190 with DSM-Deutsche Sammlung von Mikroorganismen und Zellkulturen GmbH, Mascheroder Weg 1b, D-38124 Braunschweig Germany.

EXAMPLE 11

Demonstration of the usefulness of pFG1 as a food-grade cloning vector

A 3.5 kb BamHI/SacI fragment containing the entire pepN gene (also referred to as lap gene), coding for a lysine-aminopeptidas was moved from plasmid pSTO3 (Strøman, 1992) into the multiple cloning site of pFG1 to produce a plasmid named pFG2. The transformed strain DN209/pFG2 was added to the culture collection of Chr. Hansen's Laboratorium under the name CHCC3062 and deposited on 6 May 1994 under accession No. DSM 9191 with DSM-Deutsche Sammlung von Mikroorganismen und Zellkulturen GmbH, Mascheroder Weg 1b, D-38124 Braunschweig Germany.

Cell free extracts were prepared from DN209/pFG1 and DN209/pFG2 and assayed for lysine-aminopeptidase. Enzyme activity in DN209/pFG2 was 228.3 nmoles/min/mg protein which was 4–5 fold higher than for DN209/pFG1 (48.7 nmoles/min/mg protein). Thus, introducing extra copies of the pepN gene into DN209 results in increased expression of that gene.

EXAMPLE 12

Stability of pFG-derived plasmids in milk

The β-galactosidase gene from *Leuconostoc mesenteroides* subsp. *cremoris* was inserted into pFG1 to produce pFG3. This gene was obtained from a clone named pSBl (Johansen and Kibenich, 1992a) which has been shown by DNA sequence analysis to contain the lacL and lacM genes (unpublished data). Cells containing this plasmid give blue colonies on plates containing X-gal while plasmid-free cells give white colonies. This gives a simple method for detecting plasmid loss and allows screening of many colonies for determining the stability of this plasmid.

DN209/pFG3 was grown in GM17 or in milk and plated at various times on X-gal-containing plates. Milk was supplemented with glucose and casamino acids because DN209 is plasmid free and therefor Lac⁻ and Prt⁻. The percent white colonies at various times was determined and is presented below:

| White colonies | Milk + glucose + casamino acids | GM17 |
|---|---|---|
| 0 Generations | 0.1% | 0.1% |
| 10 Generations | 0.4% | 0.5% |
| 20 Generations | 0.1% | 13.1% |
| 30 Generations | 0.1% | 8.8% |
| 40 Generations | 0.2% | 3.4% |

These results clearly demonstrate that milk is a selective medium for strains containing pFG1 derivatives, in this case pFG3. Satisfactory stability was also obtained with GM17. The decrease in percent white colonies after 20 generations is believed to be due to the accumulation of faster growing variants of DN209/pFG3.

EXAMPLE 13

Isolation and characterization of faster-growing variants of DN209/pFG1

During the course of stability studies with DN209/pFG3 as described in Example 12 above, it was noticed that faster growing variants of the strain appear to accumulate. Analysis of these variants revealed a mutation in the tRNA structural gene which would destabilize the tRNA resulting in reduced expression of the suppressor gene. Testing of DN209/pFG1 revealed the same accumulation of faster growing variants.

DN209/pFG1 was grown 45 generations in GM17, then plated on GM17 plates. Large colonies were patched to Minimal medium to identify those which had retained pFG1. Twelve mutants were isolated from a single culture. Plasmid analysis revealed that all had pFG1 and that one mutant (#12) had a reduced plasmid copy number. DNA sequence analysis of the suppressor tRNA gene revealed three classes of mutants. One class had no apparent alterations. One class had a GC to CG transversion in the promoter region while the other had a TA to CG transition (SEQ ID NO:37). Both of these are in or near the region postulated to be involved in the stringent response (Ogasawara et al., 1983, Nilsson and Johansen, 1994) and would be expected to decrease suppressor gene expression. These are illustrated below:

```
                                              C in pFG1.2
Mutants                                      | C in pFG1.1
                                             | |
Wild-type  CTTGAAATTTATGAGGGTTTTTGTAAAATATTTCTTGTCGTCATCA
              -35                -10           Stringent
```

The mutant plasmids described here could be used as the second generation food-grade vector as they have overcome a potential problem with pFG1 (i.e. a slight growth inhibition).

The class of mutants with no apparent alterations in plasmid copy number or in the suppressor gene are particularly interesting because they might contain chromosomal mutations overcoming the growth inhibition caused by PFG1. To confirm that they do not contain plasmid alterations, we electroporated DN209 with pFG1, pFG1.1 and the plasmid containing no detectable alterations (called pFG1.3).

Streaking of the resulting transformants revealed that cells containing pFG1.1 produced faster growing colonies than cells containing PFG1 and pFG1.3. Thus, a plasmid mutation is responsible for the better growth of DN209/PFG1.1, and pFG1.3 does not contain such a mutation. Clearly then, the mutation giving faster growth of the original 'DN209'/pFG1.3 must be in the DN209 chromosome. The plasmid was cured from 'DN209'/pFG1.3 resulting in a strain named GH209 which we expect to be a better host for pFG1 and the various derivatives as a chromosomal mutation in this strain overcomes the slight growth inhibition caused by pFG1.

EXAMPLE 14

The construction of a pFG-derivative expressing a lactococcal lysyl-, alanyl-, histidyl-amino peptidase (PEPC)

A 2.3 kb gene coding for lysyl-, alanyl-, histidyl-amino peptidase (pepc) was isolated from *Lactococcus lactis* strain CHCC377 (Chr. Hansen's Laboratorium's culture collection).

1. Cloning and characterization of the pepC gene

The pepC gene was cloned by PCR technique. The complete nucleotide (nt) sequence of the pepC gene has been determined (see below) and an open reading frame (ORF) of 1308 nt is predicted to encode a polypeptide of 436 amino acids (aa) (approx. 52 kDa; pI 5.92). The 5'-flanking region contains no hydrophobic sequence encoding a potential leader sequence suggesting an intracellular localization of PEPC like all aminopeptidases so far known in Lactococcus. A consensus promoter and elements (−35, −10, and SD) that are involved in transcription and in the initiation of translation in Lactococcus are present. The gene also contains an inverted repeat downstream from the TAA stopcodon, which might be involved in termination of transcription.

Sequence homology was found with the proteolytic enzymes of the cysteine proteinase family (enzymes with an active thiol group), which includes papain, aleurain and cathepsins B and H. No (significant) homology was found between PEPC and papain outside the regions encoding the active site.

The pepC gene is not (over-)expressed in *E. coli* as e.g. pepN, when a plasmid (pUC18) harbouring the pepC gene is transformed into *E. coli* strain DH5α. No enzyme activity could be measured and no extra or "heavier" band in the 50 kDa region could be detected after acrylamide gel-electrophoresis, when compared to a control strain without the gene fragment. Whether this is due to the assay procedure employed or is caused by a non-functional pepC promoter in *E. coli*, is not known at present.

The sequence comprising pepc is shown below (SEQ ID NO:38:

```
  1 ATGACAGTAA  CATCAGATTT  CACACAAAAA  CTCTACGAAA  ATTTTGCAGA
 51 AAATACAAAA  TTGCGTGCGG  TGGAAAATGC  CGTGACTAAA  AATGGTTTGC
101 TTTCATCACT  CGAAGTCCGT  GGTTCACATG  CAGCAAATTT  GCCTGAGTTT
151 TCAATTGACT  TGACAAAAGA  CCCTGTAACG  AATCAAAAAC  AATCTGGTCG
201 TTGCTGGATG  TTTGCTGCTT  TGAACACTTT  CCGTCATAAA  TTTATCAATG
251 AATTTAAAAC  AGAGGATTTT  GAGTTTTCAC  AAGCTTACAC  TTTCTTCTGG
301 GATAAATATG  AAAAATCAAA  CTGGTTCATG  GAACAAATTA  TTGGTGATAT
351 TGAAATGGAC  GATCGTCGTT  TGAAATTCCT  TTTACAAACA  CCACAACAAG
401 ATGGCGGCCA  ATGGGATATG  ATGGTTGCAA  TTTTTGAAAA  ATATGGAATT
451 GTTCCCAAAG  CTGTTTATCC  TGAATCACAA  GCTTCAAGTA  GCTCACGTGA
501 ATTGAATCAA  TACTTGAATA  AACTACTCCG  TCAAGATGCT  GAAATTTTGC
551 GTTATACAAT  TGAGCAAGGT  GGAGATGTTC  AAGCAGTTAA  AGAAGAACTT
```

-continued

| 601 | TTGCAAGAAG | TCTTTAATTT | CCTTGCGGTA | ACTTTAGGTT | TGCCACCACA |
|-----|------------|------------|------------|------------|------------|
| 651 | AAATTTTGAA | TTTGCTTTCC | GTAATAAAGA | TAATGAATAC | AAAAAATTTG |
| 701 | TTGGTAGTCC | AAAAGAATTT | TACAATGAAT | ATGTTGGAAT | TGATTTGAAT |
| 751 | AATTATGTGT | CAGTAATCAA | TGCTCCAACT | GCTGACAAAC | CTTATAATAA |
| 801 | GAGCTACACA | GTTGAGTTTC | TTGGAAATGT | TGTCGGTGGT | AAAGAAGTGA |
| 851 | AACATTTGAA | TGTTGAAATG | GACCGCTTTA | AAAAATTGGT | CATTGCCCAA |
| 901 | ATGCAAGCTG | GTGAAACAGT | TTGGTTTGGT | TGTGACGTGG | GTCAAGAATC |
| 951 | AAATCGTTCA | GCAGGACTTT | TGACAATGGA | TTCTTATGAT | TTCAAATCTT |
| 1001 | CATTGGATAT | TGAATTTACT | CAAAGCAAAG | CAGGACGTCT | TGACTATGGT |
| 1051 | GAGTCGTTGA | TGACGCATGC | CATGGTTTTA | GCGGGTGTTG | ATTTAGATGC |
| 1101 | TGACGGAAAT | TCAACTAAAT | GGAAAGTTGA | AAATTCATGG | GGTAAAGATG |
| 1151 | CGGGTCAAAA | AGGATATTTT | GTTGCCTCTG | ATGAATGGAT | GGATGAATAT |
| 1201 | ACTTATCAAA | TTGTTGTCCG | TAAAGACCTT | TTAACTGAAG | AAGAATTGGC |
| 1251 | TGCTTACGAA | GAGAAACCTC | AAGTACTTCT | ACCATGGGAC | CCAATGGGTG |
| 1301 | CTTTAGCTTA | A | | | |

2. Construction and characterization of a pFG-derivative containing the CHCC377 pepC gene The CHCC377 pepC gene was inserted into the polylinker of pFG1 to obtain pFG4. DN209 was transformed with this plasmid and the peptidase activity of DN209/pFG4 was compared with that of DN209/pFG1 (control). The PEPC activity of the control was 3.1 nmoles/min/mg protein but that of DN209/pFG4 was 12.5 nmoles/min/mg protein, i.e. about a 4-fold increase of activity.

A strain of DN209/pFG4 was deposited on 6 May 1994 under accession No. DSM 9192 with DSM-Deutsche Sammlung von Mikroorganismen und Zellkulturen GmbH, Mascheroder Weg 1b, D-38124 Braunschweig Germany.

pUC18 and it was found that the gene product was not overproduced in E. coli and it was confirmed that the gene product is a dipeptidase. In the following the gene is referred to as pepR and the gene product as PEPR. Below is shown a 1419 bp sequence comprising the pepR sequence (SEQ ID NO:39):

| 1 | ATGACAACTA | TTGATTTTAA | AGCTGAAGTT | GAAAAGCGTA | AGGACGCTTT |
|-----|------------|------------|------------|------------|------------|
| 51 | GATGGAAGAT | TTGTTTAGCC | TTTTGCGCAT | TGATTCTGCA | ATGGATATGG |
| 101 | AACATGCAGA | TGCTGAAAAT | CCATTTGGCC | CTGGTCCAAG | AAAAGCTTTG |
| 151 | GATGCATTCT | TGAAAATTGC | CGAACGTGAT | GGTTATACAA | CTAAAAATTA |
| 201 | TGATAACTAT | GTTGGACATT | TTGAAATATGA | AAACGGAGCA | AATGCTGATG |
| 251 | CCGAAGTTCT | CGGAATTATT | GGTCACTTAG | ATGTTGTTCC | TGCTGGTTCC |
| 301 | GGTTGGGATT | CAAATCCATT | TGAGCCAGAA | ATCCGTAATG | GGAATCTCTA |
| 351 | TGCTCGTGGT | GCTTCTGATG | ATAAAGGACC | AACAGTTGCA | TGTTACTATG |
| 401 | CACTCAAATT | TTTGAAAGAA | CTTAATCTTC | CATTATCTAA | AAAAATCCGT |
| 451 | TTCATCGTTG | GTACAAACGA | AGAAACAGGT | TGGGCAGATA | TGGATTACTA |
| 501 | CTTTGAGCAC | TGTGAATTGC | CGTTGCCTGA | TTTTGGTTTC | TCACCTGATG |
| 551 | CTGAGTTCCC | AATTATCAAT | GGTGAAAAAG | GGAATATCAC | AGAATATCTC |
| 601 | CATTTCTCAG | GTAAAAATGC | TGGTCAAGTT | GTTCTTCACA | GCTTTAAAGC |
| 651 | AGGTCTTGCA | GAAAATATGG | TTCCAGAATC | AGCAACTGCA | GTGATTTCAG |
| 701 | GTGCTAAAGA | TTTAGAAGCT | GCACTTGAAA | AATTTGTAGC | TGAACATGCA |
| 751 | AGCAAAAATC | TTCGTTTTGA | CCTTGAAGAG | GCTGATGGAA | AAGCAACAAT |
| 801 | TACGCTTTAT | GGTAAATCAG | CGCATGGTGC | GATGCCAGAA | AAAGGGATTA |
| 851 | ATGGAGCAAC | TTATCTTACT | TTGTTCTTGA | ATCAATTTGA | CTTTGCTGAC |
| 901 | GGTGCTGCTG | CCTTCATTAA | AGTTGGGGCT | GAAAAACTTC | TTGAAGATCA |
| 951 | TGAAGGTGAA | AAATTAGGAA | CAGCTTTTAT | TGATGAATTG | AAGGGAAATA |
| 1001 | CCTCAATGAA | TGCTGGTGTT | TGGTCATTTG | ATGAAAATGG | TGAAGGTAAA |
| 1051 | ATCGCCCTCA | ATTTCCGTTT | CCCACAAGGG | AACAGCCCAG | AGCGTATGCA |
| 1101 | AGAAATTCTT | GCTAAACTTG | ATGGGGTTGT | TGAAGTTGAA | CTTTCAAAAC |
| 1151 | ACCTCCACAC | ACCTCACTAT | GTTCCAATGT | CAGACCCACT | TGTATCAAGA |
| 1201 | TTGATTGATG | TTTATGAAAA | ACACACTGGT | CTTAAAGGCT | ATGAAACAAT |
| 1251 | CATTGGTGGT | GGAACTTTCG | GTCGTCTGTT | GGAACGTGGT | GTTGCTTATG |
| 1301 | GAGCAATGTT | TGAAGGAGAA | CCAGATTCAA | TGCACCAAGC | GAATGAAATG |
| 1351 | AAACCTGTTG | AGAATATCTA | CAAAGCGGCA | GTGATTTATG | CTGAAGCAAT |
| 1401 | TTATGAACTT | GCAAAATAA | | | |

New plasmids pFG5 and pFG6 were constructed by inserting the above 2.3 kb fragment into pFG1, in either directions.

A strain of DN209/pFG5 and of DN209/pFG6 were deposited on 6 May 1994 under accession Nos. DSM 9193 and DSM 9194, respectively, with DSM-Deutsche Sammlung von Mikroorganismen und Zellkulturen GmbH, Mascheroder Weg 1b, D-38124 Braunschweig Germany.

EXAMPLE 15

Construction of pFG derivatives containing the dipeptidase gene (pepR) from lactococcus strain NCDO712.

A HindIII fragment of 2.3 kb which overlaps the 5' end of the pepR gene was cloned and characterized by sequencing. The fragment codes for a polypeptide (PEPR) of 471 amino acids of about 52 kDa. The gene was cloned in plasmid

EXAMPLE 16

Control of gene expression and of growth in lactic acid bacteria by regulated suppression of a rep-am mutation.

The experiments described in this Example illustrate how regulation of the expression of a suppressor gene can be utilized to control expression from other genes. This control of gene expression is further extended to controlling the growth of lactic acid bacteria in different environments.

1. Bacterial strains and growth media

The Pur⁻ mutant strain *Lactococcus lactis* DN209 pur-am as described in the above Example 8 was used as host for various plasmids. The media used were M17 medium supplemented with 0.5% glucose (GM17) or the purine-free DN-medium based on the phosphate-buffered medium of Clark and Maaløe (1967). When required, antibiotics were added to the following final concentrations: chloramphenicol, 10 mg/l and erythromycin 2 mg/l. The purine compounds adenine, hypoxanthine and guanosine were added to a final concentration of 15 mg/l as described in the results.

2. Plasmids

The plasmids pFDi17 (sup⁺) (Example 6) expressing an ochre suppressor, pFDi19 (sup⁻) (Example 6) not expressing a suppressor and pAK58 rep-am) (Example 4) containing an amber mutation in the replication essential gene repb are described above.

For the experiments with regulated expression of the sup gene, the plasmid, pIAM4 was constructed in the following manner: pFDi19 contains a nonsense suppressor gene that is silent (no expression), because the sup gene lacks a promoter to direct expression. Inserting a promoter in front of the sup gene restores expression. However, the expression from the promoter located in front of the purD gene of *Lactococcus lactis* is regulated. Expression from this promoter is dependent on the accessibility of purines. If purines are available in the growth medium, expression from this promoter is repressed. However, if purines are not present in the medium the expression is derepressed. Therefore, this purD promoter was selected to direct the expression of the sup gene of pFDi19. A 850 bp EcoRI fragment that contains the *Lactococcus lactis* purD promoter was cloned into a unique EcoRI site of pFDi19 which is located just in front of the sup gene of pFDi19.

3. Construction of the experimental strains

The DN209 strain was transformed with the plasmids pFDi17 (sup⁺), pFDi19 (sup⁻) and pIAM4 (Ppursup) and transformants were selected for chloramphenicol resistance. The strains DN209/pFDi17 and DN209/pFDi19 were constructed and used as experimental control strains.

4. Results

The three strains DN209/pFDi17, DN209/pFDi19 and DN209/pIAM4 represent strains with differently expressed suppressor genes. DN209/pFDi17 contains the wildtype sup gene that is expressed more or less constitutively when grown in DN-medium with and without purines. DN209/pFDi19 contains a suppressor gene that is not expressed because the gene lacks a promoter. However, DN209/pIAM4 contains a suppressor gene that is only expressed in media without purine compounds whereas no or only minor expression of the suppressor gene is observed in media containing purines. This can be used to control the replication of the plasmid pAK58 that contains an amber mutation in the replication essential gene repB. The replication of pAK58 is therefore dependent on suppression of the amber mutation in the repB gene. If pAK58 is capable of replicating in a host strain, this strain becomes erythromycin resistant.

In the below Table 8 are shown the results of attempts to introduce pAK58 into the above-mentioned strains DN209/pFDi17, DN209/pFDi19 or DN209/pIAM4(P^pur^sup). When grown on DN-medium agar plates without purines but containing erythromycin, no transformants were obtained with DN209/pFDi19(sup⁻), whereas transformants could be obtained with both DN209/pFDi17(sup+) and DN²⁰⁹/pIAM4($P_{pur}$sup). This is in accordance with the fact that pAK58 cannot exist in host strains without a suppressor gene. However, as it can be seen, only DN209/pFDi17/pAK58 and not DN209/pIAM4/pAK58 was able to grow on media containing erythromycin and purines (DN supplemented with adenine (ad), hypoxanthine (hx) and guanosine (gu), or GM17). This is in accordance with the assumption that the suppressor gene in DN209/pIAM4 is not expressed on media containing purines and accordingly, pAK58 cannot replicate and accordingly, no erythromycin resistant transformants were obtained.

This experiment demonstrates regulated suppression, not only regulation of the expression of the suppressor gene but also regulated expression of other genes dependent on suppression and also regulation of the growth of host bacteria.

TABLE 8

Selection of DN209 strains in which transformation with pAK58 is attempted

| Strain | Number of transformants with 50 ng pAK58 selecting Ery^R and Cam^R on different media | | |
|---|---|---|---|
|  | DN | DN + ad, hx, gu | GM17 |
| DN209/pFDi17 | >10³ | >10³ | 500 |
| DN209/pFDi19 | 0 | 0 | 0 |
| DN209/pIAM4 | >10³ | 0 | 0 |

EXAMPLE 17

Construction of an amber mutation located in an essential gene.

The ftsH gene of *Escherichia coli* is essential for growth. A gene encoding a membrane protein with putative ATPase activity which is homologous to this essential *Escherichia coli* protein, FtsH was identified adjacent to the hpt gene and the trnA operon in *Lactococcus lactis* (Nilsson et al., 1994). The deduced amino acid sequence of this gene product showed full-length similarity to FtsH protein of *Escherichia coli*.

Introducing an amber mutation in this essential gene of a *Lactococcus lactis* strain will result in a strain the viability of which will depend on the expression of the suppressor gene. Accordingly, an amber mutation was introduced by polymerase-chain reaction (PCR) into codon 325 of the *Lactococcus lactis* ftsH gene and this mutant gene with its flanking regions has been cloned into the integration vector pv2 (Nilsson et al., 1994). Introducing this amber mutation into the chromosome of Lactococcus lactis will result in a strain where maintenance of a suppressor gene is essential on all media. Furthermore, the growth of such a strain can be controlled with regulated suppression as it is explained in Example 16.

EXAMPLE 18

Procedure for selecting lactic acid bacterial mutants which are not capable of growth in milk Mutagenesis of *Lactococcus lactis* strain CHCC2281 was performed by treating a 10 ml outgrown culture in M17 medium with 300 μl EMS (Sigma #M0880) for 2.5h at 30° C.

The mutagenized culture was distributed into ten test tubes and 10 ml M17 medium was added to each tube and growth allowed to continue at 30° C. for 18h.

From each of the ten cultures 1.5 ml was used to inoculate 30 ml M17 medium and growth allowed to continue at 30° C. until OD at 600 nm ($OD_{600}$) was between 0.2 and 0.3 when cells from 1.0 ml of each culture were harvested by centrifugation, washed twice in 0.9% sterile NaCl solution and resuspended in 20 ml milk.

The ten cultures in milk were incubated at 30° C. for 2 h. Ampicillin was then added at a concentration of 100 µg/ml to each and incubation continued for 5 h at 30° C. 2 units of penicillinase (Sigma #P0389) was added to each culture and incubation continued for 30 minutes. Dilutions were plated on M17 agar plates to obtain single colonies, and the plates were incubated at 30° C.

Colonies were screened for the ability to grow on milk agar plates. 200 colonies from each of the enriched cultures were screened and the number of mutants unable to grow on milk agar was between 10 and 40. All enrichments produced mutants with the desired phenotype.

All mutants except one was subsequently found to be $lac^-$ mutants as they were able to grow on milk agar plates supplemented with glucose. Presumably, the $lac^-$ mutants result from the loss of the plasmid carrying the lac genes.

The one mutant strain which was unable to grow on milk+glucose agar plates was not suppressed to the wildtype by introduction of the plasmid pFDi18 and accordingly the mutation was not a nonsense mutation.

However, desired nonsense mutants can be isolated if the enrichment for $lac^-$ strains is avoided. This can easily be achieved by the addition of glucose to the milk used in the enrichment cultures and on the milk agar plates. If milk is substituted by milk+glucose in the enrichment medium, the above procedure will exclusively yield mutants of the same class as the one unable to grow on milk+glucose. Screening of a collection of this type of mutants will (as screening of $pur^-$ mutants) yield some mutants which can be suppressed by the cloned suppressor gene.

Accordingly, it is contemplated that the above selection procedure, when modified as indicated by enriching the mutated culture in a medium containing milk and glucose, will provide the appropriate means for effectively selecting lactic acid bacterial mutant strains which as a result of nonsense mutation has lost the capability of growing in milk. Such strains will be useful as the basis for constructing, in accordance with the present invention, lactic acid bacterial strains which can be contained to milk.

EXAMPLE 19

Providing a derivative of pFDi10 which is capable of replicating in a Leuconostoc species In order to demonstrate the generality of the herein disclosed techniques in lactic acid bacteria a derivative of pFDi10 (Example 1) was constructed which can be used in members of the Leuconostoc genus, a lactic acid bacterial genus which is fairly distantly related to Lactococcus. This construction procedure includes identification of a Leuconostoc plasmid replicon, addition of that replicon to pFDi10 and introducing this derivative into Leuconostoc. It is contemplated that such an approach is suitable for any plasmid-containing lactic acid bacterium.

1. Identification of a Leuconostoc replicon

*Leuconostoc mesenteroides* subsp. *cremoris* DB1165 contains 4 plasmids (Johansen and Kibenich, 1992). Two of these plasmids contain a single BglII site allowing the cloning of the entire plasmid as a BglII fragment. Cloning was into the BglII site in the polylinker of pIC19H (Marsh et al., 1984). pBL1 contains the 8.3 kb plasmid from DB1165 and pBL2 contains the 3.6 kb plasmid cloned in pIC19H. A 2.2 kb BamHI-ClaI fragment from pVA891 (Macrina et al., 1983) containing the $Ery^R$ gene was inserted into pBL1 and pBL2 to give pAK109 and pAK110, respectively.

*Lactococcus lactis* strain MG1363, *Leuconostoc lactis* strain DB1164, *Leuconostoc cremoris* strain DB 1165 were electroporated with pAK109 and pAK110. Colonies were obtained in two electroporations and MG1363/pAK109 and DB1164/pAK109 were purified and the presence of pAK109 was confirmed by plasmid analysis. Thus, pAK109 replicates in *E. coli, Lactococcus lactis* and *Leuconostoc lactis,* and the BglII site of the 8.3 kb plasmid can be used for cloning without interference with replication.

2. Construction of pFDi10 derivatives which can replicate in Leuconostoc spp.

The polylinker of pFDi10 contains a unique BamHI site. The above 8.3 kb plasmid was inserted into that site as a BamHI fragment producing two clones, pAK116 and pAK117, differing only with regard to the orientation of the inserted DNA fragment. Thus, these plasmids contain all of the pFDi10 (i.e. including replicons for *E. coli* and Lactococcus, a gene for tetracycline resistance and nonsense mutations in genes for resistance to chloramphenicol and erythromycin) and a replicon which is functional in Leuconostoc spp. These plasmids have a size of about 20.5 kb (FIG. 7).

3. Strategy for introduction of PAK116 or PAK117 into Leuconostoc spp.

Attempts to introduce pAK116 or pAK117 into *Leuconostoc lactis* DB1164 or *Leuconostoc mesenteroides* subsp. *cremoris* DB1165 by electroporation were unsuccessful, presumably due to the size of this plasmid and the low efficiency of electroporation of Leuconostoc.

However it is known (David et al., 1989; Dessart et al., 1991) that Leuconostoc spp. can be successfully transformed and accordingly, it is contemplated that transformants of Leuconostoc spp. such as those mentioned above, containing pAK116 or pAK117 can be obtained by mating MG1363/pAK116 or MG1363/pAK117 (which can be constructed by electroporation) with DB1164 or DB 1165 and selecting for resistance to vancomycin (200 µg/ml) and tetracycline (10 µg/ml). DB1164 and DB 1165, like other dairy Leuconostoc strains are inherently resistant to vancomycin, whilst MG1363/pAK116 and MG1363/pAK117 are sensitive to that antibiotic. Resistance to tetracycline is conferred by pAK116 or pAK117.

It is contemplated that the above pFDi10 derivatives can form the basis for selecting Leuconostoc species carrying suppressor genes by using essentially the same procedures as detailed in Example 2 including guidance from standard microbiological methods which are well-known to those skilled in the art.

REFERENCES

1. Andachi Y., F. Yamao, A. Muto and S. Osawa 1989: Codon recognition patterns as deduced from sequences of the complete set of transfer RNA species in *Mycoplasma capricolum.* J. Mol. Biol. 209, 37–54.

2. Austin and Wierzhicki 1983. Plasmid 10, 73–81.

3. Campbell, A. 1965: The steric effect in lysogenization by bacteriophage lambda. I. Lysogenisation by a partially diploid strain of *E. coli* K12. Virology 27, 329.

4. Clark, D. J. and O. Maaløe 1967: DNA replication and the division cycle in *Escherichia coli.* J. Mol. Biol. 23, 99–112.

5. David, S., G. Simons and W. M. Vos 1989: Plasmid transformation by electroporation of *Leuconostoc paramesenteroides* and its use in molecular cloning. Appl. Environ. Microbiol. 55, 1483–1489.

6. Demerec, M., E. A. Adelberg, A. J. Clark and P. E. Hartman 1966: A proposal for a uniform nomenclature in bacterial genetics. Genetics 54, 61–76.

7. Dessart, S. R. and L. R. Steenson 1991: High frequency intergeneric and intrageneric conjugal transfer of drug resistance plasmids in *Leuconostoc mesenteroides* ssp. *cremoris*. J. Dairy Sci. 74, 2912–2919.

8. Deno H. and M. Sugiura 1983: The nucleotide sequence of tRNA Ser (GCU) and tRNA (UUG) genes from tobacco chloroplasts. Nucleic Acids Res. 11, 8407–8414.

9. Eggertson, G. and D. Söll 1988: Transfer ribonucleic acid-mediated suppression of termination codons in *Escherichia coli.* Microbiol. Rev., 52, 354–374.

10. Gasson, M. J. 1983: Plasmid complements of *Streptococcus lactis* NCDO712 and other lactis streptococci after protoplast induced curing. J. Bacteriol. 154, 1–9.

11. Hanic-Joyce, P. J. and M. W. Gray 1990: Processing of transfer RNA precursors in a wheat mitochondrial extract. J. Biol. Chem. 265, 13782–13791.

12. Hayes F., C. Daly and G. F. Fitzgerald 1990: Identification of the minimal replicon of *Lactococcus lactis* subsp. *lactis* UC317 plasmid pCI305. Appl. Environ. Microbiol. 56, 202–209.

13. Hill, C., G. Venema, C. Daly and G. F. Fitzgerald 1988: Cloning and characterization of the tetracycline resistance determinant of and several promoters from within the conjugative transposon Tn919. Appl. Environ. Microbiol. 54, 1230–1236.

14. Hiratsuka, J., H. Shimada, R. Whittier, T. Ishibashi, M. Sakamoto, M. Mori, C. Kondo, Y. Honji, C. R. Sun, B. Y. Meng, Y. Q. Li, A. Kanno, Y. Nishizawa, A. Hirai, K. Shinozaki and M. Sugiura 1989: The complete sequence of the rice (Oryza sativa) chloroplast genome: intermolecular recombination between distinct tRNA genes accounts for a major plastid DNA inversion during the evolution of cereals. Mol. Gen. Genet. 217, 185.194.

15. Holo, H. and I. F. Nes 1989: High-frequency transformation, by electroporation, of *Lactococcus lactis* subsp *cremoris* grown with glycine in osmotically stabilized media. Appl. Environ. Microbiol. 55, 3119–3123.

16. Israelsen, H. and E. B. Hansen 1993: Insertion of Transposon Tn917 Derivatives into the *Lactococcus lactis* subsp *lactis* Chromosome. Appl. Environ. Microbiol. 59, 21–26.

17. Jahns, A., A. Schafer, A. Geiss and M. Teuber 1991: Identification, cloning and sequencing of the replication region of *Lactococcus lactis* subsp. *lactis* biovar *diacetylactis* Bu2 citrate plasmid pSL2. FEMS Microbiol. Lett. 80, 253–258.

18. Johansen, E. and A. Kibenich 1992: Characterization of Leuconostoc isolates from commercial mixed-strain mesophilic starter cultures. J Dairy Sci. 75, 1186–1191

19. Johansen, E. and A. Kibenich 1992a: Isolation and characterization of IS1165, an insertion sequence of *Leuconostoc mesenteroides* subsp. *cremoris* and other lactic acid bacteria,. Plasmid 27, 200–206.

20. Karabin, G. D. and R. B. Hallick 1983: Euglena gracilis chloroplast transfer RNA transcription units. Nucleotide sequence analysis of a tRNAThr-tRNAGly-tRNAMet-tRNASer-tRNAGln gene cluster. J. Biol. Chem. 258, 5512–5518.

21. Ma, D. P., Y. W. Yang and S. Hasnain 1989: Nucleotide sequence of *Chlamydomonas reinhardtii* mitochondrial genes coding for tRNA gln (UUG) and tRNA met (CAU). Nucleic Acids Res. 17, 1256–1256.

22. Macrina, F. L., R. P. Evans, J. A. Tobian and D. L. Hartley 1983: Novel shuttle plasmid vehicles for Escherichia—Streptococcus transgenic cloning. Gene 25, 145–150.

23. Maid, U., R. Steinmueller and K. Zetsche 1992: Structure and expression of a plasmid-encoded groEl homologous heatshock gene in athermophilic unicellular red alga. Curr. Genet. 21, 521–525.

24. Marsh, J. L., M. Erfle and E. J. Wykes. 1984: The pIC plasmid and phage vectors with versatile cloning sites for recombinant selection by insertional inactivation. Gene 32, 481–485.

25. Nagano, Y., R. Matsuno and Y. Sasaki 1991: Sequence and transcriptional analysis of the gene cluster trnQ-zfpA-psaI-ORF231-petA in pea chloroplasts. Curr. Genet. 20, 431–436.

26. Nakajima, N., H. Ozeki and Y. Shimura 1981: Organisation and structure of an *E. coli* tRNA operon containing seven tRNA genes. Cell 23, 239–249.

27. Neuhard, J. and P. Nygaard 1987: Purines and Pyrimidines. In Neidhardt PC (ed), *Escherichia coli* and *Salmonella typhimurium.* American Society for Microbiology, Washington, D.C., pp 445–473

28. Neuhaus, H. 1989: Nucleotide sequence of the chloroplast genes fro tRNA Gln and the 4 kD K polypeptide of photosystem II from mustard (S.a.). Nucleic Acids Res. 17, 444–444.

29. Nilsson, D. and B. Hove-Jensen 1987: Phosphoribosylpyrophosphate synthetase of *Bacillus subtilis.* Cloning, characterization and chromosomal mapping of the prs gene. Gene 53, 247–255

30. Nilsson, D. and E. Johansen 1994: A conserved sequence in tRNA ans rRNA promoters of *Lactococcus lactis.* Biochim. Biophys. Acta. Submitted for publication.

31. Nilsson, D., Lauridsen, A. A., Tomoyasu, T. & Ogura, T. 1994. A *Lactococcus lactis* gene encodes a membrane protein with putative ATPase activity that is homologous to the essential *Escherichia coli* gene product. Microbiology, in press.

32. Nygaard, P. 1983: Utilization of preformed purine bases and nucleosides. In Munch-Petersen A (ed), Metabolism of nucleotides, nucleosides and nucleobases in microorganisms. Academic Press, Inc., New York, pp 27–93

33. Oda, K., K. Yamato, E. Ohta, Y. Nakamura, N. Nozato, T. Kohchi T., Y. Ogura, T. Kanegae, K. Akashi and K. Ohyama 1992: Gene organization deduced from the complete sequence of liverwort Marchantia polymorpha mitochondrial DNA. J. Mol. Biol. 223, 1–7.

34. Oda, K., K. Yamato, E. Ohta, Y. Nakamura, M. Takemura, N. Nozato, K. Akashi and K. Ohyama 1992: Transfer RNA genes in the mitochondrial genome from a liverwort, Marchantia polymorpha: the absence of chloroplast-like tRNAs. Nucleic Acids Res. 20, 3773–3777.

35. Ohyama, K., H. Fukuzama, T. Kohchi, T. Sano, H. Shirai, K. Umesono, Y. Shiki, M. Takeuchi, Z. Chang, S. I. Aota, H. Inokuchi and H. Ozeki 1988: Structure and organization of Marchantia polymorpha Chloroplast genome. I. cloning and gene identification. J. Mol. Biol. 203, 281–298.

36. Ogasawara, N., S. Moriya and H. Yoshikawa 1983: Structure and organization of rRNA operons in the region of the replication region of the Bacillus subtilis chromosome. Nucleic Acids Res. 11, 6301–6316.

37. Pedersen, M. L., K. R. Arnved and E. Johansen 1994: Genetic analysis of the minimal replicon of the *Lactococcus lactis* subsp. *lactis* biovar diacetylactis citrate plasmid. Submitted for publication.

38. Pittet, A. C. and H. Hottinger 1989: Sequence of an hexameric tRNA gene cluster associated with rRNA genes in *Lactobacillus bulgaricus*. Nucl. Acid. Res. 17, 4873.

39. Ryan, M. J., E. L. Brown, R. Belangaje, H. G. Khorana and H. J. Fritz 1980: Cloning of two chemically synthesised genes for a precursor to the su$^+$3 suppressor tRNA$^{Tyr}$ in D. Söll; J. N. Abelson and P. R. Schimmel (eds.) Transfer RNA: Biological Aspects. Cold Spring Harbor Laboratory, Cold Spring Harbor, N.Y., pp. 245–258.

40. Sambrook, J., E. F. Fritsch and T. Maniatis 1989: Molecular cloning: A Laboratory Manual. Cold Spring Harbor Laboratory, Cold Spring Harbor, N.Y.

41. Siemeister, G., C. Buchholz and W. Hachtel 1990: Genes for the plastid elongation factor Tu and ribosomal protein s7 and six tRNA genes on the 73 kb DNA from *Astasia longa* that resembles the cloroplast DNA of Euglena. Mol. Gen. Genet. 220, 425–432.

42. Silhavy, T. J., M. L. Berman and L. W. Enquist 1984: Experiments with gene fusions. Cold Spring Harbor Laboratory, Cold Spring Harbor, N.Y.

43. Simeneau, P., R. Wenzel, R. Herrmann and P. C. Hu 1990: Nucleotide sequence of a tRNA cluster from *Mycoplasma pneumoniae*. Nucleic Acids Res. 18, 2814–2814.

44. Strøman, P. 1992: Sequence of a gene (lap) encoding a 95.3-kDa aminopeptidase from *Lactococcus lactis* ssp. *cremoris* Wg2. Gene 113, 107–112.

45. Thorbjarnadöttir, S., H. Uemura, T. Dingermann, T. Rafnar, S. Thorsteindöttir, D. Söll and G. Eggertson 1985: *Escerichia coli* supH suppressor: Temperature-sensitive missense suppression caused by anticodon change in tRNA$_2$$^{Ser}$. J. Bacteriol. 161, 207–211.

46. Tsudzuki, J., K. Nakashima, T. Tsudzuki, J. Hiratsuka, M. Shibata, T. Wakasugi and M. Sugiura 1992: Chloroplast DNA of black pine retains a residual inverted repeat lacking rRNA genes: nucleotide sequences of trnQ, trnK, psbA, trnI and trnH and the absence of rps16. Mol. Gen. Genet. 232, 206–214.

47. Wawrousek, E. F., N. Narasimhan and J. N. Hansen 1984: Two large clusters with thirty-seven transfer RNA genes adjacent to ribosomal RNA gene sets in *Bacillus subtilis*. J. Biol. Chem. 259, 3694–3702.

48. Wolfe, K. H., C. W. Morden, S. C. Ems and J. D. Palmer 1992: Rapid revolution of the plastid translational apparatus in a nonphotosynthetic plant: loss or accelerated sequence evolution of tRNA and ribosomal protein genes. J. Mol. Evol. 35, 304–317.

49. Yanase, H., H. Fukushi, N. Ueda, Y. Maeda, A. Toyoda and K. Tonomura 1991: Cloning, sequencing and characterization of the intracellular in envertase gene from *Zymomonas mobilis*. Agric. Biol. Chem. 55, 1383–1390.

50. Yaniv M. and W. R. Folk 1975: The nucleotide sequences of the two glutamine transfer ribonucleic acids from *Escherichia coli*. J. Biol. Chem. 250, 3243–3253.

---

We claim:

1. A method of isolating a nonsense suppressor-encoding lactic acid bacterium, comprising the steps of
   (i) mutagenizing a replicon capable of replicating in a lactic acid bacterium, said replicon comprising a gene encoding a selectable marker which is expressible in the lactic acid bacterium,
   (ii) selecting from the mutagenized replicon of (i) a replicon containing a nonsense mutation in the gene encoding the selectable marker,
   (iii) mutagenizing a lactic acid bacterium which does not encode a nonsense suppressor,
   (iv) introducing the replicon of step (ii) into said mutagenized lactic acid bacterium, and
   (v) selecting from the mutagenized lactic acid bacterium of (iv) a nonsense suppressor-encoding transformed lactic acid bacterium in which the selectable marker is expressed.

2. A method according to claim 1 wherein the transformed lactic acid bacterium in a further step is cured of the replicon introduced in step (iv).

3. A method according to claim 1 wherein the nonsense suppressor is selected from a group consisting of an amber suppressor and an ochre suppressor.

4. A method according to claim 1 wherein the nonsense suppressor-encoding gene is a tRNA-encoding gene.

5. A method according to claim 1 wherein the nonsense-suppressor gene is located on the chromosome.

6. A method according to claim 1 wherein the replicon being mutagenized in step (i) is selected from a plasmid and a bacteriophage.

7. A method according to claim 1 wherein the selectable marker of the replicon being mutagenized in step (i) is selected from antibiotic resistance and auxotrophy.

8. A method of isolating a nonsense suppressor-encoding lactic acid bacterium, comprising the steps of
   (i) mutagenizing a replicon without nonsense mutations but containing a selectable marker, which plasmid is inherently capable of replicating in a lactic acid bacterium,
   (ii) selecting from step (i) a replicon containing a nonsense mutation rendering the replicon incapable of replicating, (iii) mutagenizing a lactic acid bacterium which does not encode a nonsense suppressor, (iv) introducing into said mutagenized lactic acid bacterium the replicon of step (ii), and (v) selecting a transformed lactic acid bacterium in which the introduced replicon is capable of replicating.

9. A method according to claim 8 wherein the transformed lactic acid bacterium in a further step is cured of the replicon introduced in step (iv).

10. A method according to claim 8 wherein the replicon is selected from a plasmid and a bacteriophage.

11. A method according to claim 10 wherein the replicon being mutagenized in step (i) is a wildtype plasmid isolated from a lactic acid bacterium.

12. A method according to claim 10 wherein the replicon is a citrate plasmid.

13. An isolated pure culture of a lactic acid bacterium comprising a gene coding for a nonsense suppressor.

14. A culture according to claim 13 wherein the gene coding for a nonsense suppressor is a gene coding for tRNA.

15. A culture according to claim 13 wherein the gene coding for the nonsense suppressor is located on the chromosome.

16. A culture according to claim 13 wherein the gene coding for a nonsense suppressor is located on a non-chromosomal replicon.

17. A culture according to claim 16 wherein the gene is isolated from a lactic acid bacterium.

18. A culture according to claim 13 wherein the nonsense suppressor is selected from the group consisting of an amber suppressor and an ochre suppressor.

19. A culture according to claim 13 which further comprises a nonsense mutation being suppressible by the nonsense suppressor.

20. A culture according to claim 19 wherein the nonsense mutation is located on a replicon different from the one containing the gene coding for a nonsense suppressor.

21. A culture according to claim 13 wherein the lactic acid bacterium is selected from Lactococcus spp., Streptococcus spp., Lactobacillus spp., Leuconostoc spp., Pediococcus spp. and Bifidobacterium spp.

22. A culture according to claim 21 wherein the lactic acid bacterium is *Lactococcus lactis*.

23. A culture according to claim 13 wherein the suppressor is one suppressing a nonsense mutation which in the absence of a nonsense suppressor capable of suppressing the mutation, confers auxotrophy.

24. A culture according to claim 23 wherein the nonsense mutation is in a gene involved in the synthesis of purine nucleotides from their precursors.

25. A culture according to claim 24 wherein the lactic acid bacterium is a pur mutant.

26. A culture according to claim 13 containing at least $10^9$ colony forming units of the lactic acid bacterium per g.

27. A culture according to claim 26 which is selected from a frozen culture and a freeze-dried culture.

28. A culture according to claim 13 wherein the gene coding for a nonsense suppressor is under the control of a regulatable promoter.

29. A culture according to claim 28 wherein the regulatable promoter is a promoter not naturally related to the gene.

30. A composition comprising an isolated pure culture of a lactic acid bacterium as defined in claim 20, and a carrier.

31. A composition according to claim 30 containing at least $10^9$ colony forming units of the lactic acid bacterium per g.

32. A plasmid comprising lactobacterial DNA and capable of replicating in a lactic acid bacterium, the plasmid comprising a gene coding for a nonsense suppressor.

33. A plasmid according to claim 32, wherein the gene coding for a nonsense supressor is isolated from the chromosome of a lactic acid bacterium.

34. A plasmid according to claim 32 wherein the gene coding for a nonsense suppressor is a gene coding for tRNA.

35. A plasmid according to claim 34 wherein the nonsense mutation suppressor is selected from the group consisting of an amber suppressor and an ochre suppressor.

36. A method of confining an extrachromosoal replicon capable of replicating in lactic acid bacteria to a first kind of lactic acid bacterial cells, where said replicon could be naturally transferred to a second kind of lactic acid bacterial cells, which method comprises providing the first kind of lactic acid bacterial cells as cells containing a nonsense suppressor-encoding gene, the cells being transformed with the replicon in the form of a nonsense mutant having lost its capability of replicating in lactic acid bacterial cells, the gene product of the nonsense suppressor-encoding gene being capable of restoring the capability of the replicon to replicate in lactic acid bacterial cells whereby, if a cell of the second kind which does not contain a nonsense suppressor gene encoding a gene product capable of restoring the capability of the nonsense mutant of the replicon to replicate in lactic acid bacteria, receives said extrachromosomal replicon, the replicon will not replicate in the second kind of lactic acid bacterial cell.

37. A method according to claim 36 wherein the first kind of lactic acid bacterial cells contains the nonsense suppressor-encoding gene in the chromosome.

38. A method according to claim 36 wherein the first kind of lactic acid bacteria is selected from lactococcus spp., Streptococcus spp., Lactobacillus spp., Leuconostoc spp., Pediococcus spp. and Bifidobacterium spp.

39. A method according to claim 38 wherein the first kind of lactic acid bacteria is *Lactococcus lactis*.

40. A method according to claim 36 wherein the first kind of lactic acid bacterial cells-is present in a composition comprising a mixture of the first kind of cells and at least one second kind of lactic acid bacterial cells not containing a nonsense suppressor gene encoding a gene product capable of restoring the capability of the nonsense mutant of the replicon to replicate in lactic acid bacteria.

41. A method according to claim 40 wherein the first and second kind of lactic acid bacterial cells are cultivated in a food product selected from a dairy product, a vegetable product, a meat product and a bakery product.

42. A culture according to claim 20 wherein the lactic acid bacterium comprises a vector consisting of DNA from a lactic acid bacterium or a plasmid naturally occurring in a lactic acid bacterium, comprising a selectable marker, a replication region and at least one restriction site.

43. A culture according to claim 42 wherein the selectable marker is the suppressor gene.

44. A culture according to claim 43 wherein the vector is pFG1.

45. A culture according to claim 43 wherein the promoter for the suppressor gene is mutated whereby the expression of the gene is altered to an extent where the growth of the lactic acid bacterium is not decreased relative to that of a bacterium hosting a vector in which the promoter for the suppressor gene is not mutated.

46. A culture according to claim 42 wherein the vector further comprises an inserted gene coding for a desired gene product.

47. A culture according to claim 46 wherein the gene product is a peptidase.

48. A starter culture for the prepartion of a food product selected from the group consisting of a dairy product, a vegetable product, a meat product and a bakery product, comprising a composition according to claim 30.

49. A method for using a composition according to claim 30 for the preparation of a starter culture-treated food product, comprising:

combining said composition with said food product under conditions where the starter culture produces lactic acid, wherein said food product is selected from the group consisting of a dairy product, a vegetable product, a meat product and a bakery product.

* * * * *

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GGAGCCATGG   CAGAGTGGTA   ATGCAACGGA   CTCTAAATCC   GTCGAACCGT   GTAAAGCGGC      60

GCAGGGGTTC   AAATCCCCTT   GACTCCTTA                                              89
```

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

```
TGAATTCAGA   GGTTTGATGA   CTTTGACC                                               28
```

( 2 ) INFORMATION FOR SEQ ID NO:3:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:3:

GGAATTCCTA ACAAAAGACT ATTAACGC 28

( 2 ) INFORMATION FOR SEQ ID NO:4:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:4:

AAACTCTAGA GCAAGTATTC G 21

( 2 ) INFORMATION FOR SEQ ID NO:5:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:5:

CTTGCTCTAG AGTTTTTGTA G 21

( 2 ) INFORMATION FOR SEQ ID NO:6:

( i ) SEQUENCE CHARACTERISTICS:
    ( A ) LENGTH: 33 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 1..33

( x ) PUBLICATION INFORMATION:
    ( A ) AUTHORS: Macrina, F.L.
                   Evans, R.P.
                   Tobian, J.A.
                   Hartley, D.L.
    ( B ) TITLE: Novel shuttle plasmid vehicles for
                 Escherichia - Streptococcus transgenic cloning
    ( C ) JOURNAL: Gene
    ( D ) VOLUME: 25
    ( F ) PAGES: 145-150
    ( G ) DATE: 1983

( x i ) SEQUENCE DESCRIPTION: SEQ ID NO:6:

GAA CTA CAA AAA CTC AAT AGC AAG TAT TCG ATT 33
Glu Leu Gln Lys Leu Asn Ser Lys Tyr Ser Ile
 1               5                   1 0

( 2 ) INFORMATION FOR SEQ ID NO:7:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

Glu Leu Gln Lys Leu Asn Ser Lys Tyr Ser Ile
 1           5                   10

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

GCTAGAGTAA GTAGTT                                                           16

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

CCTTTACCTT GTCTACAAAC C                                                     21

( 2 ) INFORMATION FOR SEQ ID NO:10:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

AATTGCGACA GTGTCTTCAT TTGAGGCTGC TTTAGAAGAA GCAATCAAGG AATATAATCT           60
ATCTATTTAA AGAGATTATA AAAAATTATT GATATTTCTT TGAAATAAAT AAGTTAAAAC          120
TTGAAATTTA TGAGGGTTTT TGGTAAAATA TTTCTTGTCG TCATCAAGCG ATCTTGGGGT          180
ATAGCCAAGC GGTAAGGCAA GGGACTTTAA CTCCCTCATG CGTTGGTTCG AATCCAGCTA          240
CCCCAGTAAA AAAACTTTAA AGGAAACGTT GTTTCCTTTT TTCTTTTTAC TAAAATATGA          300

( 2 ) INFORMATION FOR SEQ ID NO:11:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

TTTGTATAAA TATGCGTTTT TTGTTTTAGT TATTCTTATT TCATATTATT TCAGGAAGGT           60

| | | | | | |
|---|---|---|---|---|---|
| AATTAACTAT | GGTATAATGA | AATTAGATAA | GGGAGCGGAG | CCATGGCAGA | GTGGTAATGC | 120
| AACGGACTCT | AAATCCGTCG | AACCGTGTAA | AGCGGCGCAG | GGGTTCAAAT | CCCCTTGACT | 180
| CCTTATAAGT | AGAGTTCTTT | ATTCTCAACT | CTATTATATA | AGAAAAATGA | TAGTATTGAA | 240
| TACGCTTACT | CCTTTTCCTC | CTGTATGTAT | AAGATTACAT | CAGGAGGTTT | TTTTATTCAA | 300

( 2 ) INFORMATION FOR SEQ ID NO:12:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

| | | | | | |
|---|---|---|---|---|---|
| TGGAGTATAG | CCAAGTGGTA | AGGCATCGGC | CTTTGATGCC | GAGAAACAAA | GGTTCGAATC | 60
| CTTTTACTCC | AG | | | | | 72

( 2 ) INFORMATION FOR SEQ ID NO:13:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

| | | | | | |
|---|---|---|---|---|---|
| TGGAGTATAG | CCAAGTGGTA | AGGCATCGGC | CTTTGATGCC | GAGAAACAAA | GGTTCGAATC | 60
| CTTTTACTCC | AG | | | | | 72

( 2 ) INFORMATION FOR SEQ ID NO:14:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

| | | | | | |
|---|---|---|---|---|---|
| TGGGGCATAG | CCAAGTGGTA | AGGCATTGGA | CTTTGACTCC | AAGATGCATG | GGTTCGAATC | 60
| CTATTGCCCC | AG | | | | | 72

( 2 ) INFORMATION FOR SEQ ID NO:15:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

| | | | | | |
|---|---|---|---|---|---|
| TGGGGCGTGG | CCAAGTGGTA | AGGCAGCGGG | TTTTGATCCC | GTTATTCGGA | GGTTCGAATC | 60
| CTTCCGTCCC | AGCCA | | | | | 75

( 2 ) INFORMATION FOR SEQ ID NO:16:

( i ) SEQUENCE CHARACTERISTICS:

(A) LENGTH: 72 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:16:

TGGGGCGTGG CCAAGTGGTA AGGCAGCGGG TTTTGGTCCC GTTACTCGGA GGTTCGAATC      60

CTTCCGTCCC AG      72

(2) INFORMATION FOR SEQ ID NO:17:

(i) SEQUENCE CHARACTERISTICS:
          (A) LENGTH: 72 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:17:

TGGGGCGTGG CCAAGTGGTA AGGCAACGGG TTTTGGTCCC GCTATTCGGA GGTTCGAATC      60

CTTCCGTCCC AG      72

(2) INFORMATION FOR SEQ ID NO:18:

(i) SEQUENCE CHARACTERISTICS:
          (A) LENGTH: 72 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:18:

TGGGGCGTAG CCAAGCGGTA AGGCAACGGG TTTTGGTCCC GCTATTCGGA GGTTCGAATC      60

CTTCCGTCCC AG      72

(2) INFORMATION FOR SEQ ID NO:19:

(i) SEQUENCE CHARACTERISTICS:
          (A) LENGTH: 72 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:19:

TGGGGCGTGG CTAAGTGGTA AGGCAACGGG CTTTGGTCCC GCTATTCGTA GGTTCGAATC      60

CTTCCGTCCC AG      72

(2) INFORMATION FOR SEQ ID NO:20:

(i) SEQUENCE CHARACTERISTICS:
          (A) LENGTH: 72 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:20:

TGGGGCGTGG CCAAGCGGTA AGGCGGCGGG TTTTGGTCCC GTGATTCGGA GGTTCGAATC      60

CTTCCGTCCC AG      72

( 2 ) INFORMATION FOR SEQ ID NO:21:

( i ) SEQUENCE CHARACTERISTICS:
           ( A ) LENGTH: 72 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:21:

```
TGGGGCGTGG  CCAAGCGGTA  AGGCAGCAGG  TTTTGATCCT  GTTATTCGGA  GGTTCGAATC      60
CTTCCGTCCC  AG                                                              72
```

( 2 ) INFORMATION FOR SEQ ID NO:22:

( i ) SEQUENCE CHARACTERISTICS:
           ( A ) LENGTH: 72 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:22:

```
TGGGGCGTCG  CCAAGTGGTA  AGGCTGCAGG  TTTTGGTCCT  GTTATTCGGA  GGTTCGAATC      60
CTTCCGTCCC  AG                                                              72
```

( 2 ) INFORMATION FOR SEQ ID NO:23:

( i ) SEQUENCE CHARACTERISTICS:
           ( A ) LENGTH: 72 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:23:

```
TGAGGCGTAG  CCAAGTGGTA  AGGCAACGGG  TTTTGGCCCT  GTCATTCGGA  GGTTCGAATC      60
CTCCCGCCTC  AG                                                              72
```

( 2 ) INFORMATION FOR SEQ ID NO:24:

( i ) SEQUENCE CHARACTERISTICS:
           ( A ) LENGTH: 72 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:24:

```
TGGGGCGTAG  CCAAGCGGTA  AGGCAACGGG  TTTTGATCCC  GTCATGCGCA  GGTTCGAATC      60
CTGCCGCCCC  AA                                                              72
```

( 2 ) INFORMATION FOR SEQ ID NO:25:

( i ) SEQUENCE CHARACTERISTICS:
           ( A ) LENGTH: 72 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:25:

TGAGGTGTAG CCAAGCGGTA AGGCAGCGGA CTTTGACTCC GCGATTCGTA GGTTCGAATC    60

CTACCACCTC AG    72

( 2 ) INFORMATION FOR SEQ ID NO:26:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TGGGGTGTAG CCAAGTGGTA AGGTAACAGG TTTTGACCCT GTAATGCGAG GGTTCAAATC    60

CTTCCACCTC AG    72

( 2 ) INFORMATION FOR SEQ ID NO:27:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

TGGGGTATCG CCAAGCGGTA AGGCACCGGT TTTTGATACC GGCATTCCCT GGTTCGAATC    60

CAGGTACCCC AGCCA    75

( 2 ) INFORMATION FOR SEQ ID NO:28:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

TGGGGTATCG CCAAGCGGTA AGGCACCGGA TTCTGATTCC GGCATTCCGA GGTTCGAATC    60

CTCGTACCCC AGCCA    75

( 2 ) INFORMATION FOR SEQ ID NO:29:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

TGGGCTATAG CCAAGCGGTA AGGCAAGGGA CTTTGACTCC CTCATGCGCC GGTTCGAATC    60

CTGCTAGCCC AACCA    75

( 2 ) INFORMATION FOR SEQ ID NO:30:

( i ) SEQUENCE CHARACTERISTICS:
        ( A ) LENGTH: 75 base pairs
        ( B ) TYPE: nucleic acid (C) STRANDEDNESS: single
                (D) TOPOLOGY: linear (ii) MOLECULE TYPE: DNA (genomic)

(xi) SEQUENCE DESCRIPTION: SEQ ID NO:30:

TGGGATGTAG CCAAGCGGTA AGGCAATAGA CTTTGACTCT ATCATGCGAT GGTTCGATCC        60

CATCCATCCC AGCCA        75

(2) INFORMATION FOR SEQ ID NO:31:

(i) SEQUENCE CHARACTERISTICS:
                (A) LENGTH: 72 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:31:

TGGGCTATAG CCAAGCGGTA AGGCAACGGA CTTTGACTCC GTCATGCGTT GGTTCGAATC        60

CAGCTAGCCC AG        72

(2) INFORMATION FOR SEQ ID NO:32:

(i) SEQUENCE CHARACTERISTICS:
                (A) LENGTH: 72 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:32:

TGGGGTATAG CCAAGCGGTA AGGCAAGGGA CTTTAACTCC CTCATGCGTT GGTTCGAATC        60

CAGCTACCCC AG        72

(2) INFORMATION FOR SEQ ID NO:33:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (xi) SEQUENCE DESCRIPTION: SEQ ID NO:33:

CGAATTCATA AATGCTTTCC CCTATTC        27

(2) INFORMATION FOR SEQ ID NO:34:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:34:

CGAATTCTTG AAATTTATGA GGGTTTTTGG        30

(2) INFORMATION FOR SEQ ID NO:35:

(i) SEQUENCE CHARACTERISTICS:
                (A) LENGTH: 69 base pairs
                (B) TYPE: nucleic acid
                (C) STRANDEDNESS: double
                (D) TOPOLOGY: linear ( x i ) SEQUENCE DESCRIPTION: SEQ ID NO:35:

| GAATTCCCGG | GGATCCGTCG | ACCTGCAGCC | AAGCTTTCGC | GAGCTCGAGA | TCTAGATATC | 60 |
| GATGAATTC | | | | | | 69 |

( 2 ) INFORMATION FOR SEQ ID NO:36:

( i ) SEQUENCE CHARACTERISTICS:
        ( A ) LENGTH: 2006 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

| GAATTCCCGG | GGATCCGTCG | ACCTGCAGCC | AAGCTTTCGC | GAGCTCGAGA | TCTAGATATC | 60 |
| GATGAATTCC | TAACAAAAGA | CTATTAACGC | TTAATTCTTC | ATTTTTTCTT | GTCGATTTTC | 120 |
| GGTCGGTTGA | ACTTTTTTTA | TTTTTGTTAG | TCTTTTTTTG | ATAAACTTTT | GTTCTTCAAG | 180 |
| GTTTAGGACG | ATCGAACCAC | TATTGTTTTT | TTGTCGATTT | TCGGTCGGCA | AAAACTTTAA | 240 |
| ATGGTATTGA | ACGGTCTGTT | TAGCTAGTCC | TAGCTCGTCC | GCCAACTCTT | TATCGTTTT | 300 |
| TAAGTCTTCA | CTCATGGTTT | AAGTCCTGCC | TTTTAACCGT | TGGCAGATAT | TGTTCAATGG | 360 |
| CTTTTTTAAG | ATATTTCGCT | ACATTACGTT | TAGAATAGGC | TTCTTTTTG | CTGGCAACAT | 420 |
| AAGACAAGTG | GTCTTTGACA | CCATTTAGCC | CTCTTAATTC | TTTCAGTTCG | TCATAAAGCG | 480 |
| GATAAACATT | CTTCTGTAAG | CCTACCATTG | TGGCTGTATC | CATAATATCA | TTCATGCCAA | 540 |
| TTAAGAAATT | TTCAGATAAA | AGTCTTGTAT | ATTTACTTTC | CATTGCCTGT | TTTAGTAAGT | 600 |
| CAGCTTCATT | TCTTGATTTT | TGCTTTTTAT | CGTCTTGATA | GTCTTTATCT | CCCAACTTGT | 660 |
| AACTGTTATC | GTCTGCCATG | CGTTTCTTCT | CAATATGAAA | GACAATAGAG | TCAATGCTCC | 720 |
| GCCCTGCTTT | CTTTTTCTCA | TAGGTTACAT | TAAAAGAGGT | GTGAGCGTTG | ATTTCTTCAA | 780 |
| TTGCTTTTTT | TAATACTCTA | GTTTCAAAAT | GGGGAAAATG | TTGATGTTCA | TTTATTGTAT | 840 |
| CAGTTATTTC | TCGCAATTCT | TTCACTTTTA | TTGAGGGGTT | GCGGTAGGAT | TCCACTTGTT | 900 |
| CAACTCTCCG | TCCCCCTTTC | ACGCTGTAAT | GTTCGTATTG | GTTATAATTC | ATGGATAACC | 960 |
| AACGATACAA | AATAATCGAA | TACTTGCTAT | TGAGTTTTTG | TAGTTCGGAA | ATTTTATATT | 1020 |
| GAGTAAATTC | TGCCTTTAAA | TCAATCAGAT | AGGGCATAAT | GGCTTGGTCA | AAACGTATTG | 1080 |
| TTACTTCATC | GTTATAATCG | TTCCATTTTA | CATAAGGAAT | AGGCACAATG | CTTTCATACT | 1140 |
| CAATACCTAG | TTTCTTATCA | GCTTTAATAT | TGAAAAGGC | TTGCTTTTGC | ATATAATTAA | 1200 |
| CTGCTTCTTT | GAATTGACTA | TGCTTACTGC | TAGACGATAC | TTCAAAAAAT | TTAAAAGTT | 1260 |
| CAGATTTTAA | AAGATAAACA | GTATTATTTT | TTGGGGGTTC | TTCGGTATCA | ATACAAGACA | 1320 |
| CGGCTAACTC | AAACATTTTT | AAAGCTGTTT | TTTGCATTTT | AGCCACACTT | TGAATTAAAG | 1380 |
| CGTTATGCTC | CACTACTTTG | CGTTTTCTA | ATTCATTCAA | GGTCAGCACC | TGCTTTTGTT | 1440 |
| TGTTTTGTTT | TTCTGGTATA | ATCATAGTAT | AAATACGCTC | CTTTGCGTGT | TTTAGTAGTA | 1500 |
| GCATAGAGAA | AGTCATTTCA | TAGTGAGTTT | TCTCTATGCT | TTTATTATAC | TATATACAGT | 1560 |
| ACACAAATAC | AAAAGTCGTG | CTGTGTACAT | CGATTTTGT | GACTCTATAC | ATCGATTTTT | 1620 |
| GTGACTCTAT | ACATCGATTT | TTGTGACTGT | TTAATTTCTA | TAACTAGCGA | AAACACTGCC | 1680 |
| TTTTTTTTCA | CGCAAAAGAA | CAAAAGATTA | AATATATAT | GATAAATATA | TAGTAGGCTT | 1740 |
| CGCCTTTTTT | TATTTTTTTC | AAAAATTTAA | AACCAAAGGT | CAAAGTCATC | AAACCTCTGA | 1800 |
| ATTCTTGAAA | TTTATGAGGG | TTTTTGGTAA | AATATTTCTT | GTCGTCATCA | AGCGATCTTG | 1860 |
| GGGTATAGCC | AAGCGGTAAG | GCAAGGGACT | TTAACTCCCT | CATGCGTTGG | TTCGAATCCA | 1920 |

GCTACCCCAG TAAAAAAACT TTAAAGGAAA CGTTGTTTCC TTTTTTCTTT TTACTAAAAT 1980

ATGATAGAAT AGGGGAAAGC ATTTAT 2006

( 2 ) INFORMATION FOR SEQ ID NO:37:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( x i ) SEQUENCE DESCRIPTION: SEQ ID NO:37:

CTTGAAATTT ATGAGGGTTT TTGTAAAATA TTTCTTGTCG TCATCA 46

( 2 ) INFORMATION FOR SEQ ID NO:38:

( i ) SEQUENCE CHARACTERISTICS:
( A ) LENGTH: 1311 base pairs
( B ) TYPE: nucleic acid
( C ) STRANDEDNESS: single
( D ) TOPOLOGY: linear ( x i ) SEQUENCE DESCRIPTION: SEQ ID NO:38:

ATGACAGTAA CATCAGATTT CACACAAAAA CTCTACGAAA ATTTTGCAGA AAATACAAAA 60

TTGCGTGCGG TGGAAAATGC CGTGACTAAA AATGGTTTGC TTTCATCACT CGAAGTCCGT 120

GGTTCACATG CAGCAAATTT GCCTGAGTTT TCAATTGACT TGACAAAAGA CCCTGTAACG 180

AATCAAAAAC AATCTGGTCG TTGCTGGATG TTTGCTGCTT TGAACACTTT CCGTCATAAA 240

TTTATCAATG AATTTAAAAC AGAGGATTTT GAGTTTTCAC AAGCTTACAC TTTCTTCTGG 300

GATAAATATG AAAAATCAAA CTGGTTCATG GAACAAATTA TTGGTGATAT TGAAATGGAC 360

GATCGTCGTT TGAAATTCCT TTTACAAACA CCACAACAAG ATGGCGGCCA ATGGGATATG 420

ATGGTTGCAA TTTTTGAAAA ATATGGAATT GTTCCCAAAG CTGTTTATCC TGAATCACAA 480

GCTTCAAGTA GCTCACGTGA ATTGAATCAA TACTTGAATA AACTACTCCG TCAAGATGCT 540

GAAATTTTGC GTTATACAAT TGAGCAAGGT GGAGATGTTC AAGCAGTTAA AGAAGAACTT 600

TTGCAAGAAG TCTTTAATTT CCTTGCGGTA ACTTTAGGTT TGCCACCACA AAATTTTGAA 660

TTTGCTTTCC GTAATAAAGA TAATGAATAC AAAAAATTTG TTGGTAGTCC AAAAGAATTT 720

TACAATGAAT ATGTTGGAAT TGATTTGAAT AATTATGTGT CAGTAATCAA TGCTCCAACT 780

GCTGACAAAC CTTATAATAA GAGCTACACA GTTGAGTTTC TTGGAAATGT TGTCGGTGGT 840

AAAGAAGTGA AACATTTGAA TGTTGAAATG GACCGCTTTA AAAAATTGGT CATTGCCCAA 900

ATGCAAGCTG GTGAAACAGT TTGGTTTGGT TGTGACGTGG GTCAAGAATC AAATCGTTCA 960

GCAGGACTTT TGACAATGGA TTCTTATGAT TTCAAATCTT CATTGGATAT TGAATTTACT 1020

CAAAGCAAAG CAGGACGTCT TGACTATGGT GAGTCGTTGA TGACGCATGC CATGGTTTTA 1080

GCGGGTGTTG ATTTAGATGC TGACGGAAAT TCAACTAAAT GGAAAGTTGA AAATTCATGG 1140

GGTAAAGATG CGGGTCAAAA AGGATATTTT GTTGCCTCTG ATGAATGGAT GGATGAATAT 1200

ACTTATCAAA TTGTTGTCCG TAAAGACCTT TTAACTGAAG AAGAATTGGC TGCTTACGAA 1260

GAGAAACCTC AAGTACTTCT ACCATGGGAC CCAATGGGTG CTTTAGCTTA A 1311

( 2 ) INFORMATION FOR SEQ ID NO:39:

( i ) SEQUENCE CHARACTERISTICS:
( A ) LENGTH: 1419 base pairs
( B ) TYPE: nucleic acid
( C ) STRANDEDNESS: single ( D ) TOPOLOGY: linear ( x i ) SEQUENCE DESCRIPTION: SEQ ID NO:39:

```
ATGACAACTA  TTGATTTTAA  AGCTGAAGTT  GAAAAGCGTA  AGGACGCTTT  GATGGAAGAT    60
TTGTTTAGCC  TTTTGCGCAT  TGATTCTGCA  ATGGATATGG  AACATGCAGA  TGCTGAAAAT   120
CCATTTGGCC  CTGGTCCAAG  AAAAGCTTTG  GATGCATTCT  TGAAAATTGC  CGAACGTGAT   180
GGTTATACAA  CTAAAAATTA  TGATAACTAT  GTTGGACATT  TTGAATATGA  AAACGGAGCA   240
AATGCTGATG  CCGAAGTTCT  CGGAATTATT  GGTCACTTAG  ATGTTGTTCC  TGCTGGTTCC   300
GGTTGGGATT  CAAATCCATT  TGAGCCAGAA  ATCCGTAATG  GAATCTCTA   TGCTCGTGGT   360
GCTTCTGATG  ATAAAGGACC  AACAGTTGCA  TGTTACTATG  CACTCAAATT  TTTGAAAGAA   420
CTTAATCTTC  CATTATCTAA  AAAAATCCGT  TTCATCGTTG  GTACAAACGA  AGAAACAGGT   480
TGGGCAGATA  TGGATTACTA  CTTTGAGCAC  TGTGAATTGC  CGTTGCCTGA  TTTTGGTTTC   540
TCACCTGATG  CTGAGTTCCC  AATTATCAAT  GGTGAAAAAG  GAATATCAC   AGAATATCTC   600
CATTTCTCAG  GTAAAAATGC  TGGTCAAGTT  GTTCTTCACA  GCTTTAAAGC  AGGTCTTGCA   660
GAAAATATGG  TTCCAGAATC  AGCAACTGCA  GTGATTTCAG  GTGCTAAAGA  TTTAGAAGCT   720
GCACTTGAAA  AATTTGTAGC  TGAACATGCA  AGCAAAAATC  TTCGTTTTGA  CCTTGAAGAG   780
GCTGATGGAA  AAGCAACAAT  TACGCTTTAT  GGTAAATCAG  CGCATGGTGC  GATGCCAGAA   840
AAAGGGATTA  ATGGAGCAAC  TTATCTTACT  TTGTTCTTGA  ATCAATTTGA  CTTTGCTGAC   900
GGTGCTGCTG  CCTTCATTAA  AGTTGGGGCT  GAAAAACTTC  TTGAAGATCA  TGAAGGTGAA   960
AAATTAGGAA  CAGCTTTTAT  TGATGAATTG  AAGGGAAATA  CCTCAATGAA  TGCTGGTGTT  1020
TGGTCATTTG  ATGAAAATGG  TGAAGGTAAA  ATCGCCCTCA  ATTTCCGTTT  CCCACAAGGG  1080
AACAGCCCAG  AGCGTATGCA  AGAAATTCTT  GCTAAACTTG  ATGGGGTTGT  TGAAGTTGAA  1140
CTTTCAAAAC  ACCTCCACAC  ACCTCACTAT  GTTCCAATGT  CAGACCCACT  TGTATCAAGA  1200
TTGATTGATG  TTTATGAAAA  ACACACTGGT  CTTAAAGGCT  ATGAAACAAT  CATTGGTGGT  1260
GGAACTTTCG  GTCGTCTGTT  GGAACGTGGT  GTTGCTTATG  GAGCAATGTT  TGAAGGAGAA  1320
CCAGATTCAA  TGCACCAAGC  GAATGAAATG  AAACCTGTTG  AGAATATCTA  CAAAGCGGCA  1380
GTGATTTATG  CTGAAGCAAT  TTATGAACTT  GCAAAATAA                            1419
```